US011261225B2

(12) United States Patent
Dunbrack et al.

(10) Patent No.: US 11,261,225 B2
(45) Date of Patent: Mar. 1, 2022

(54) CHIMERA OF BONE MORPHOGENIC PROTEIN 2 AND THE MÜLLERIAN-INHIBITING SUBSTANCE TYPE II RECEPTOR BINDING REGION OF MÜLLERIAN-INHIBITING SUBSTANCE

(71) Applicants: THE RESEARCH INSTITUTE OF FOX CHASE CANCER CENTER, Philadelphia, PA (US); RABD BIOTECH, LLC, Hatboro, PA (US)

(72) Inventors: Roland L. Dunbrack, Philadelphia, PA (US); Jared Adolf-Bryfogle, Philadelphia, PA (US); Gregory P. Adams, Hatboro, PA (US); Matthew K. Robinson, Blue Bell, PA (US)

(73) Assignee: INSTITUTE FOR CANCER RESEARCH, Philadelphia, PA (US)

( * ) Notice: Subject to any disclaimer, the term of this patent is extended or adjusted under 35 U.S.C. 154(b) by 0 days.

(21) Appl. No.: 16/483,944

(22) PCT Filed: Feb. 12, 2018

(86) PCT No.: PCT/US2018/017799

§ 371 (c)(1),
(2) Date: Aug. 6, 2019

(87) PCT Pub. No.: WO2018/148649

PCT Pub. Date: Aug. 16, 2018

(65) Prior Publication Data

US 2020/0010523 A1 Jan. 9, 2020

Related U.S. Application Data

(60) Provisional application No. 62/457,383, filed on Feb. 10, 2017.

(51) Int. Cl.

| | |
|---|---|
| ***C07K 14/51*** | (2006.01) |
| ***A61K 38/18*** | (2006.01) |
| ***A61K 38/22*** | (2006.01) |
| ***A61K 45/06*** | (2006.01) |
| ***C07K 14/575*** | (2006.01) |

(52) U.S. Cl.

CPC .......... *C07K 14/51* (2013.01); *A61K 38/1875* (2013.01); *A61K 38/22* (2013.01); *A61K 45/06* (2013.01); *C07K 14/575* (2013.01); *C07K 2319/00* (2013.01)

(58) Field of Classification Search

CPC .... A61K 38/1875; A61K 38/22; A61K 45/06; C07K 14/51; C07K 14/575; C07K 2319/00

See application file for complete search history.

(56) References Cited

U.S. PATENT DOCUMENTS

| | | | |
|---|---|---|---|
| 5,618,924 | A | 4/1997 | Wang et al. |
| 8,658,135 | B2 | 2/2014 | O'Connor-McCourt et al. |
| 2010/0221777 | A1 | 9/2010 | Choe et al. |

FOREIGN PATENT DOCUMENTS

| | | | |
|---|---|---|---|
| WO | 2010/099219 | A2 | 9/2010 |
| WO | 2012/166712 | A1 | 12/2012 |
| WO | 2015/041718 | A1 | 3/2015 |
| WO | 2017/123556 | A1 | 7/2017 |

OTHER PUBLICATIONS

Renlund et al. c-Jun N-terminal kinase inhibitoe II activates mullerian inhibiting substance type II receptor-mediated signal transduction. Endocrinology, 149:108-115, 2008 (Year: 2008).*
MacLaughlin et al. Müllerian Inhibiting Substance/anti-Müllerian hormone: a potential therapeutic agent for human ovarian and other cancers. Future Oncol. Mar. 2010; 6(3): 391-405) (Year: 2010).*
Renlund et al. Endocrinology, 149:108-115, 2008 (Year: 2008).*
Chin et al. Cancer Research 51. 2101-2106. Apr. 15, 1991 (Year: 1991).*
Beck et al. 2016, Cell Reports 16, 657-671 (Year: 2016).*
MacLaughlin et al. Future Oncol. Mar. 2010; 6(3): 391-405 (Year: 2010).*
Renlund, et al., "c-Jun N-terminal kinase inhibitor II (SP600125) activates Mullerian inhibiting substance type II receptor-mediated signal transduction" Endocrinology (2008) 149(1):108-15.

* cited by examiner

*Primary Examiner* — Vanessa L. Ford
*Assistant Examiner* — Sandra E Dillahunt
(74) *Attorney, Agent, or Firm* — Robert C. Netter, Jr.; Dann, Dorfman, Herrell & Skillman

(57) ABSTRACT

Recombinant proteins that comprise a bone morphogenic protein 2 backbone onto which was grafted a Müllerian-inhibiting substance type II receptor binding region of the Müllerian-inhibiting substance protein are provided. These proteins bind to this receptor on the surface of epithelial cancer cells, and induce apoptosis of such cells. These proteins are useful, for example, in the treatment of cancers such as ovarian, uterine, endometrial, fallopian tube, breast, prostate, and lung cancers.

24 Claims, 3 Drawing Sheets

Specification includes a Sequence Listing.

SEQUENCE LISTING

<160> NUMBER OF SEQ ID NOS: 58

<210> SEQ ID NO 1
<211> LENGTH: 114
<212> TYPE: PRT
<213> ORGANISM: Homo sapiens

<400> SEQUENCE: 1

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg
```

<210> SEQ ID NO 2
<211> LENGTH: 112
<212> TYPE: PRT
<213> ORGANISM: Homo sapiens

<400> SEQUENCE: 2

```
Ala Gln Arg Ser Ala Gly Ala Thr Ala Ala Asp Gly Pro Cys Ala Leu
1               5                   10                  15

Arg Glu Leu Ser Val Asp Leu Arg Ala Glu Arg Ser Val Leu Ile Pro
            20                  25                  30

Glu Thr Tyr Gln Ala Asn Asn Cys Gln Gly Val Cys Gly Trp Pro Gln
        35                  40                  45

Ser Asp Arg Asn Pro Arg Tyr Gly Asn His Val Val Leu Leu Leu Lys
    50                  55                  60

Met Gln Val Arg Gly Ala Ala Leu Ala Arg Pro Pro Cys Cys Val Pro
65                  70                  75                  80

Thr Ala Tyr Ala Gly Lys Leu Leu Ile Ser Leu Ser Glu Glu Arg Ile
                85                  90                  95

Ser Ala His His Val Pro Asn Met Val Ala Thr Glu Cys Gly Cys Arg
            100                 105                 110
```

<210> SEQ ID NO 3
<211> LENGTH: 115
<212> TYPE: PRT
<213> ORGANISM: Artificial Sequence
<220> FEATURE:
<223> OTHER INFORMATION: Variant 2 mature

<400> SEQUENCE: 3

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Gly
        35                  40                  45

Trp Pro Gln Ser Asp Arg Asn Pro Arg Tyr Gly Asn His Val Val Leu
    50                  55                  60

Leu Leu Lys Met Gln Val Arg Gly Ala Ala Leu Ala Arg Pro Pro Cys
65                  70                  75                  80

Cys Val Pro Thr Ala Tyr Ala Gly Lys Leu Leu Ile Ser Leu Ser Glu
                85                  90                  95

Glu Arg Ile Ser Ala His His Val Pro Asn Met Val Ala Thr Glu Cys
            100                 105                 110

Gly Cys Arg
        115
```

<210> SEQ ID NO 4
<211> LENGTH: 112
<212> TYPE: PRT
<213> ORGANISM: Artificial Sequence
<220> FEATURE:
<223> OTHER INFORMATION: Consensus of Variant 1 and 3 mature
<220> FEATURE:
<221> NAME/KEY: VARIANT
<222> LOCATION: 23
<223> OTHER INFORMATION: Xaa is Leu or Phe
<220> FEATURE:
<221> NAME/KEY: VARIANT
<222> LOCATION: 29
<223> OTHER INFORMATION: Xaa is Val or Ile
<220> FEATURE:
<221> NAME/KEY: VARIANT
<222> LOCATION: 30
<223> OTHER INFORMATION: Xaa is Leu or Val
<220> FEATURE:
<221> NAME/KEY: VARIANT
<222> LOCATION: 31
<223> OTHER INFORMATION: Xaa is Ile or Ala
<220> FEATURE:
<221> NAME/KEY: VARIANT
<222> LOCATION: 33
<223> OTHER INFORMATION: Xaa is Glu or Pro
<220> FEATURE:
<221> NAME/KEY: VARIANT
<222> LOCATION: (34)...(34)
<223> OTHER INFORMATION: Xaa is Thr of Gly
<220> FEATURE:
<221> NAME/KEY: VARIANT
<222> LOCATION: (36)...(36)
<223> OTHER INFORMATION: Xaa is Gln or His
<220> FEATURE:
<221> NAME/KEY: VARIANT
<222> LOCATION: (38)...(38)
<223> OTHER INFORMATION: Xaa is Asn or Phe
<220> FEATURE:
<221> NAME/KEY: VARIANT
<222> LOCATION: (39)...(39)
<223> OTHER INFORMATION: Xaa is Asn or Tyr
<220> FEATURE:
<221> NAME/KEY: VARIANT
<222> LOCATION: (41)...(41)
<223> OTHER INFORMATION: Xaa is Gln or His
<220> FEATURE:
<221> NAME/KEY: VARIANT
<222> LOCATION: (43)...(43)
<223> OTHER INFORMATION: Xaa is Val or Glu

<400> SEQUENCE: 4

```
Gln Ala Lys His Lys Gln Arg Lys Arg Leu Lys Ser Ser Cys Lys Arg
1               5                   10                  15

His Pro Leu Tyr Val Asp Xaa Arg Ala Glu Arg Ser Xaa Xaa Xaa Pro
            20                  25                  30

Xaa Xaa Tyr Xaa Ala Xaa Xaa Cys Xaa Gly Xaa Cys Gly Trp Pro Gln
        35                  40                  45

Ser Asp Arg Asn Pro Arg Tyr Gly Asn His Val Val Leu Leu Leu Lys
    50                  55                  60

Met Gln Val Arg Gly Ala Ala Leu Ala Arg Pro Pro Cys Cys Val Pro
65                  70                  75                  80

Thr Ala Tyr Ala Gly Lys Leu Leu Ile Ser Leu Ser Glu Glu Arg Ile
                85                  90                  95

Ser Ala His His Val Pro Asn Met Val Ala Thr Glu Cys Gly Cys Arg
            100                 105                 110
```

<210> SEQ ID NO 5
<211> LENGTH: 113
<212> TYPE: PRT
<213> ORGANISM: Artificial Sequence
<220> FEATURE:
<223> OTHER INFORMATION: Consensus of Variants 4, 5, 6, 8, 10, and 12 mature
<220> FEATURE:
<221> NAME/KEY: VARIANT
<222> LOCATION: 83
<223> OTHER INFORMATION: Xaa is Ala or Glu
<220> FEATURE:
<221> NAME/KEY: VARIANT
<222> LOCATION: 84
<223> OTHER INFORMATION: Xaa is Tyr or Leu
<220> FEATURE:
<221> NAME/KEY: VARIANT
<222> LOCATION: 107

<223> OTHER INFORMATION: Xaa is Ala or Val
<220> FEATURE:
<221> NAME/KEY: VARIANT
<222> LOCATION: 108
<223> OTHER INFORMATION: Xaa is Thr of Glu
<220> FEATURE:
<221> NAME/KEY: VARIANT
<222> LOCATION: 109
<223> OTHER INFORMATION: Xaa is Glu or Gly

<400> SEQUENCE: 5

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Xaa Xaa Ala Gly Lys Leu Leu Ile Ser Leu Ser Glu Glu Arg
                85                  90                  95

Ile Ser Ala His His Val Pro Asn Met Val Xaa Xaa Xaa Cys Gly Cys
            100                 105                 110

Arg
```

<210> SEQ ID NO 6
<211> LENGTH: 110
<212> TYPE: PRT
<213> ORGANISM: Artificial Sequence
<220> FEATURE:
<223> OTHER INFORMATION: Consensus of Variants 7, 9, and 11 mature
<220> FEATURE:
<221> NAME/KEY: VARIANT
<222> LOCATION: 23
<223> OTHER INFORMATION: Xaa is Leu of Phe
<220> FEATURE:
<221> NAME/KEY: VARIANT
<222> LOCATION: 29
<223> OTHER INFORMATION: Xaa is Val or Ile
<220> FEATURE:
<221> NAME/KEY: VARIANT
<222> LOCATION: 30
<223> OTHER INFORMATION: Xaa is Leu or Val
<220> FEATURE:
<221> NAME/KEY: VARIANT
<222> LOCATION: 31
<223> OTHER INFORMATION: Xaa is Ile or Ala
<220> FEATURE:
<221> NAME/KEY: VARIANT
<222> LOCATION: 33
<223> OTHER INFORMATION: Xaa is Glu or Pro
<220> FEATURE:
<221> NAME/KEY: VARIANT
<222> LOCATION: (34)...(34)
<223> OTHER INFORMATION: Xaa is Thr or Gly
<220> FEATURE:
<221> NAME/KEY: VARIANT
<222> LOCATION: (36)...(36)
<223> OTHER INFORMATION: Xaa is Gln or His
<220> FEATURE:
<221> NAME/KEY: VARIANT
<222> LOCATION: (38)...(38)
<223> OTHER INFORMATION: Xaa is Asn or Phe
<220> FEATURE:
<221> NAME/KEY: VARIANT
<222> LOCATION: (39)...(39)
<223> OTHER INFORMATION: Xaa is Asn or Tyr
<220> FEATURE:

<221> NAME/KEY: VARIANT
<222> LOCATION: (41)...(41)
<223> OTHER INFORMATION: Xaa is Gln or His
<220> FEATURE:
<221> NAME/KEY: VARIANT
<222> LOCATION: (43)...(43)
<223> OTHER INFORMATION: Xaa is Val or Glu
<220> FEATURE:
<221> NAME/KEY: VARIANT
<222> LOCATION: (80)...(80)
<223> OTHER INFORMATION: Xaa is Glu or Ala
<220> FEATURE:
<221> NAME/KEY: VARIANT
<222> LOCATION: (81)...(81)
<223> OTHER INFORMATION: Xaa is Leu or Tyr
<220> FEATURE:
<221> NAME/KEY: VARIANT
<222> LOCATION: (104)...(104)
<223> OTHER INFORMATION: Xaa is Val or Ala
<220> FEATURE:
<221> NAME/KEY: VARIANT
<222> LOCATION: (105)...(105)
<223> OTHER INFORMATION: Xaa is Glu or Thr
<220> FEATURE:
<221> NAME/KEY: VARIANT
<222> LOCATION: (106)...(106)
<223> OTHER INFORMATION: Xaa is Gly or Glu

<400> SEQUENCE: 6

```
Gln Ala Lys His Lys Gln Arg Lys Arg Leu Lys Ser Ser Cys Lys Arg
1               5                   10                  15

His Pro Leu Tyr Val Asp Xaa Arg Ala Glu Arg Ser Xaa Xaa Xaa Pro
            20                  25                  30

Xaa Xaa Tyr Xaa Ala Xaa Xaa Cys Xaa Gly Xaa Cys Pro Phe Pro Leu
        35                  40                  45

Ala Asp His Leu Asn Ser Thr Asn His Ala Ile Val Gln Thr Leu Val
    50                  55                  60

Asn Ser Val Asn Ser Lys Ile Pro Lys Ala Cys Cys Val Pro Thr Xaa
65                  70                  75                  80

Xaa Ala Gly Lys Leu Leu Ile Ser Leu Ser Glu Glu Arg Ile Ser Ala
                85                  90                  95

His His Val Pro Asn Met Val Xaa Xaa Xaa Cys Gly Cys Arg
            100                 105                 110
```

<210> SEQ ID NO 7
<211> LENGTH: 112
<212> TYPE: PRT
<213> ORGANISM: Artificial Sequence
<220> FEATURE:
<223> OTHER INFORMATION: Variant 1 mature

<400> SEQUENCE: 7

```
Gln Ala Lys His Lys Gln Arg Lys Arg Leu Lys Ser Ser Cys Lys Arg
1               5                   10                  15

His Pro Leu Tyr Val Asp Leu Arg Ala Glu Arg Ser Val Leu Ile Pro
            20                  25                  30

Glu Thr Tyr Gln Ala Asn Asn Cys Gln Gly Val Cys Gly Trp Pro Gln
        35                  40                  45

Ser Asp Arg Asn Pro Arg Tyr Gly Asn His Val Val Leu Leu Leu Lys
    50                  55                  60

Met Gln Val Arg Gly Ala Ala Leu Ala Arg Pro Pro Cys Cys Val Pro
65                  70                  75                  80

Thr Ala Tyr Ala Gly Lys Leu Leu Ile Ser Leu Ser Glu Glu Arg Ile
                85                  90                  95
```

-continued

```
Ser Ala His His Val Pro Asn Met Val Ala Thr Glu Cys Gly Cys Arg
            100                 105                 110


<210> SEQ ID NO 8
<211> LENGTH: 112
<212> TYPE: PRT
<213> ORGANISM: Artificial Sequence
<220> FEATURE:
<223> OTHER INFORMATION: Variant 3 mature

<400> SEQUENCE: 8

Gln Ala Lys His Lys Gln Arg Lys Arg Leu Lys Ser Ser Cys Lys Arg
1               5                   10                  15

His Pro Leu Tyr Val Asp Phe Arg Ala Glu Arg Ser Ile Val Ala Pro
            20                  25                  30

Pro Gly Tyr His Ala Phe Tyr Cys His Gly Glu Cys Gly Trp Pro Gln
        35                  40                  45

Ser Asp Arg Asn Pro Arg Tyr Gly Asn His Val Val Leu Leu Leu Lys
    50                  55                  60

Met Gln Val Arg Gly Ala Ala Leu Ala Arg Pro Pro Cys Cys Val Pro
65                  70                  75                  80

Thr Ala Tyr Ala Gly Lys Leu Leu Ile Ser Leu Ser Glu Glu Arg Ile
                85                  90                  95

Ser Ala His His Val Pro Asn Met Val Ala Thr Glu Cys Gly Cys Arg
            100                 105                 110


<210> SEQ ID NO 9
<211> LENGTH: 110
<212> TYPE: PRT
<213> ORGANISM: Artificial Sequence
<220> FEATURE:
<223> OTHER INFORMATION: Variant 4 mature

<400> SEQUENCE: 9

Gln Ala Lys His Lys Gln Arg Lys Arg Leu Lys Ser Ser Cys Lys Arg
1               5                   10                  15

His Pro Leu Tyr Val Asp Leu Arg Ala Glu Arg Ser Val Leu Ile Pro
            20                  25                  30

Glu Thr Tyr Gln Ala Asn Asn Cys Gln Gly Val Cys Pro Phe Pro Leu
        35                  40                  45

Ala Asp His Leu Asn Ser Thr Asn His Ala Ile Val Gln Thr Leu Val
    50                  55                  60

Asn Ser Val Asn Ser Lys Ile Pro Lys Ala Cys Cys Val Pro Thr Ala
65                  70                  75                  80

Tyr Ala Gly Lys Leu Leu Ile Ser Leu Ser Glu Glu Arg Ile Ser Ala
                85                  90                  95

His His Val Pro Asn Met Val Ala Thr Glu Cys Gly Cys Arg
            100                 105                 110


<210> SEQ ID NO 10
<211> LENGTH: 110
<212> TYPE: PRT
<213> ORGANISM: Artificial Sequence
<220> FEATURE:
<223> OTHER INFORMATION: Variant 5 mature

<400> SEQUENCE: 10

Gln Ala Lys His Lys Gln Arg Lys Arg Leu Lys Ser Ser Cys Lys Arg
1               5                   10                  15

His Pro Leu Tyr Val Asp Leu Arg Ala Glu Arg Ser Val Leu Ile Pro
```

```
            20                  25                  30

Glu Thr Tyr Gln Ala Asn Asn Cys Gln Gly Val Cys Pro Phe Pro Leu
        35                  40                  45

Ala Asp His Leu Asn Ser Thr Asn His Ala Ile Val Gln Thr Leu Val
    50                  55                  60

Asn Ser Val Asn Ser Lys Ile Pro Lys Ala Cys Cys Val Pro Thr Ala
65                  70                  75                  80

Tyr Ala Gly Lys Leu Leu Ile Ser Leu Ser Glu Glu Arg Ile Ser Ala
                85                  90                  95

His His Val Pro Asn Met Val Val Glu Gly Cys Gly Cys Arg
            100                 105                 110


<210> SEQ ID NO 11
<211> LENGTH: 110
<212> TYPE: PRT
<213> ORGANISM: Artificial Sequence
<220> FEATURE:
<223> OTHER INFORMATION: Variant 6 mature

<400> SEQUENCE: 11

Gln Ala Lys His Lys Gln Arg Lys Arg Leu Lys Ser Ser Cys Lys Arg
1               5                   10                  15

His Pro Leu Tyr Val Asp Leu Arg Ala Glu Arg Ser Val Leu Ile Pro
            20                  25                  30

Glu Thr Tyr Gln Ala Asn Asn Cys Gln Gly Val Cys Pro Phe Pro Leu
        35                  40                  45

Ala Asp His Leu Asn Ser Thr Asn His Ala Ile Val Gln Thr Leu Val
    50                  55                  60

Asn Ser Val Asn Ser Lys Ile Pro Lys Ala Cys Cys Val Pro Thr Glu
65                  70                  75                  80

Leu Ala Gly Lys Leu Leu Ile Ser Leu Ser Glu Glu Arg Ile Ser Ala
                85                  90                  95

His His Val Pro Asn Met Val Val Glu Gly Cys Gly Cys Arg
            100                 105                 110


<210> SEQ ID NO 12
<211> LENGTH: 110
<212> TYPE: PRT
<213> ORGANISM: Artificial Sequence
<220> FEATURE:
<223> OTHER INFORMATION: Variant 8 mature

<400> SEQUENCE: 12

Gln Ala Lys His Lys Gln Arg Lys Arg Leu Lys Ser Ser Cys Lys Arg
1               5                   10                  15

His Pro Leu Tyr Val Asp Phe Arg Ala Glu Arg Ser Ile Val Ala Pro
            20                  25                  30

Pro Gly Tyr His Ala Phe Tyr Cys His Gly Glu Cys Pro Phe Pro Leu
        35                  40                  45

Ala Asp His Leu Asn Ser Thr Asn His Ala Ile Val Gln Thr Leu Val
    50                  55                  60

Asn Ser Val Asn Ser Lys Ile Pro Lys Ala Cys Cys Val Pro Thr Ala
65                  70                  75                  80

Tyr Ala Gly Lys Leu Leu Ile Ser Leu Ser Glu Glu Arg Ile Ser Ala
                85                  90                  95

His His Val Pro Asn Met Val Ala Thr Glu Cys Gly Cys Arg
            100                 105                 110
```

<210> SEQ ID NO 13
<211> LENGTH: 110
<212> TYPE: PRT
<213> ORGANISM: Artificial Sequence
<220> FEATURE:
<223> OTHER INFORMATION: Variant 10 mature

<400> SEQUENCE: 13

```
Gln Ala Lys His Lys Gln Arg Lys Arg Leu Lys Ser Ser Cys Lys Arg
1               5                   10                  15

His Pro Leu Tyr Val Asp Phe Arg Ala Glu Arg Ser Ile Val Ala Pro
            20                  25                  30

Pro Gly Tyr His Ala Phe Tyr Cys His Gly Glu Cys Pro Phe Pro Leu
        35                  40                  45

Ala Asp His Leu Asn Ser Thr Asn His Ala Ile Val Gln Thr Leu Val
    50                  55                  60

Asn Ser Val Asn Ser Lys Ile Pro Lys Ala Cys Cys Val Pro Thr Ala
65                  70                  75                  80

Tyr Ala Gly Lys Leu Leu Ile Ser Leu Ser Glu Glu Arg Ile Ser Ala
                85                  90                  95

His His Val Pro Asn Met Val Val Glu Gly Cys Gly Cys Arg
            100                 105                 110
```

<210> SEQ ID NO 14
<211> LENGTH: 110
<212> TYPE: PRT
<213> ORGANISM: Artificial Sequence
<220> FEATURE:
<223> OTHER INFORMATION: Variant 12 mature

<400> SEQUENCE: 14

```
Gln Ala Lys His Lys Gln Arg Lys Arg Leu Lys Ser Ser Cys Lys Arg
1               5                   10                  15

His Pro Leu Tyr Val Asp Phe Arg Ala Glu Arg Ser Ile Val Ala Pro
            20                  25                  30

Pro Gly Tyr His Ala Phe Tyr Cys His Gly Glu Cys Pro Phe Pro Leu
        35                  40                  45

Ala Asp His Leu Asn Ser Thr Asn His Ala Ile Val Gln Thr Leu Val
    50                  55                  60

Asn Ser Val Asn Ser Lys Ile Pro Lys Ala Cys Cys Val Pro Thr Glu
65                  70                  75                  80

Leu Ala Gly Lys Leu Leu Ile Ser Leu Ser Glu Glu Arg Ile Ser Ala
                85                  90                  95

His His Val Pro Asn Met Val Val Glu Gly Cys Gly Cys Arg
            100                 105                 110
```

<210> SEQ ID NO 15
<211> LENGTH: 113
<212> TYPE: PRT
<213> ORGANISM: Artificial Sequence
<220> FEATURE:
<223> OTHER INFORMATION: Variant 7 mature

<400> SEQUENCE: 15

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
```

-continued

```
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Ala Tyr Ala Gly Lys Leu Leu Ile Ser Leu Ser Glu Glu Arg
                85                  90                  95

Ile Ser Ala His His Val Pro Asn Met Val Ala Thr Glu Cys Gly Cys
            100                 105                 110

Arg


<210> SEQ ID NO 16
<211> LENGTH: 113
<212> TYPE: PRT
<213> ORGANISM: Artificial Sequence
<220> FEATURE:
<223> OTHER INFORMATION: Variant 9 mature

<400> SEQUENCE: 16

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Ala Tyr Ala Gly Lys Leu Leu Ile Ser Leu Ser Glu Glu Arg
                85                  90                  95

Ile Ser Ala His His Val Pro Asn Met Val Val Glu Gly Cys Gly Cys
            100                 105                 110

Arg


<210> SEQ ID NO 17
<211> LENGTH: 113
<212> TYPE: PRT
<213> ORGANISM: Artificial Sequence
<220> FEATURE:
<223> OTHER INFORMATION: Variant 11 mature

<400> SEQUENCE: 17

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ala Gly Lys Leu Leu Ile Ser Leu Ser Glu Glu Arg
                85                  90                  95

Ile Ser Ala His His Val Pro Asn Met Val Val Glu Gly Cys Gly Cys
            100                 105                 110
```

Arg

<210> SEQ ID NO 18
<211> LENGTH: 396
<212> TYPE: PRT
<213> ORGANISM: Homo sapiens

<400> SEQUENCE: 18

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
370 375 380

Tyr Gln Asp Met Val Val Glu Gly Cys Gly Cys Arg
385 390 395

<210> SEQ ID NO 19
<211> LENGTH: 560
<212> TYPE: PRT
<213> ORGANISM: Homo sapiens

<400> SEQUENCE: 19

Met Arg Asp Leu Pro Leu Thr Ser Leu Ala Leu Val Leu Ser Ala Leu
1 5 10 15

Gly Ala Leu Leu Gly Thr Glu Ala Leu Arg Ala Glu Glu Pro Ala Val
20 25 30

Gly Thr Ser Gly Leu Ile Phe Arg Glu Asp Leu Asp Trp Pro Pro Gly
35 40 45

Ser Pro Gln Glu Pro Leu Cys Leu Val Ala Leu Gly Gly Asp Ser Asn
50 55 60

Gly Ser Ser Ser Pro Leu Arg Val Val Gly Ala Leu Ser Ala Tyr Glu
65 70 75 80

Gln Ala Phe Leu Gly Ala Val Gln Arg Ala Arg Trp Gly Pro Arg Asp
85 90 95

Leu Ala Thr Phe Gly Val Cys Asn Thr Gly Asp Arg Gln Ala Ala Leu
100 105 110

Pro Ser Leu Arg Arg Leu Gly Ala Trp Leu Arg Asp Pro Gly Gly Gln
115 120 125

Arg Leu Val Val Leu His Leu Glu Glu Val Thr Trp Glu Pro Thr Pro
130 135 140

Ser Leu Arg Phe Gln Glu Pro Pro Pro Gly Gly Ala Gly Pro Pro Glu
145 150 155 160

Leu Ala Leu Leu Val Leu Tyr Pro Gly Pro Gly Pro Glu Val Thr Val
165 170 175

Thr Arg Ala Gly Leu Pro Gly Ala Gln Ser Leu Cys Pro Ser Arg Asp
180 185 190

Thr Arg Tyr Leu Val Leu Ala Val Asp Arg Pro Ala Gly Ala Trp Arg
195 200 205

Gly Ser Gly Leu Ala Leu Thr Leu Gln Pro Arg Gly Glu Asp Ser Arg
210 215 220

Leu Ser Thr Ala Arg Leu Gln Ala Leu Leu Phe Gly Asp Asp His Arg
225 230 235 240

Cys Phe Thr Arg Met Thr Pro Ala Leu Leu Leu Leu Pro Arg Ser Glu
245 250 255

Pro Ala Pro Leu Pro Ala His Gly Gln Leu Asp Thr Val Pro Phe Pro
260 265 270

Pro Pro Arg Pro Ser Ala Glu Leu Glu Glu Ser Pro Pro Ser Ala Asp
275 280 285

Pro Phe Leu Glu Thr Leu Thr Arg Leu Val Arg Ala Leu Arg Val Pro
290 295 300

Pro Ala Arg Ala Ser Ala Pro Arg Leu Ala Leu Asp Pro Asp Ala Leu
305 310 315 320

Ala Gly Phe Pro Gln Gly Leu Val Asn Leu Ser Asp Pro Ala Ala Leu
325 330 335

Glu Arg Leu Leu Asp Gly Glu Glu Pro Leu Leu Leu Leu Leu Arg Pro

```
            340                 345                 350

Thr Ala Ala Thr Thr Gly Asp Pro Ala Pro Leu His Asp Pro Thr Ser
        355                 360                 365

Ala Pro Trp Ala Thr Ala Leu Ala Arg Arg Val Ala Ala Glu Leu Gln
    370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Leu Ala Leu Cys Pro Gly Gly Pro Gly
                405                 410                 415

Gly Leu Gly Asp Pro Leu Arg Ala Leu Leu Leu Leu Lys Ala Leu Gln
            420                 425                 430

Gly Leu Arg Val Glu Trp Arg Gly Arg Asp Pro Arg Gly Pro Gly Arg
        435                 440                 445

Ala Gln Arg Ser Ala Gly Ala Thr Ala Ala Asp Gly Pro Cys Ala Leu
    450                 455                 460

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
                485                 490                 495

Ser Asp Arg Asn Pro Arg Tyr Gly Asn His Val Val Leu Leu Leu Lys
            500                 505                 510

Met Gln Val Arg Gly Ala Ala Leu Ala Arg Pro Pro Cys Cys Val Pro
        515                 520                 525

Thr Ala Tyr Ala Gly Lys Leu Leu Ile Ser Leu Ser Glu Glu Arg Ile
    530                 535                 540

Ser Ala His His Val Pro Asn Met Val Ala Thr Glu Cys Gly Cys Arg
545                 550                 555                 560


<210> SEQ ID NO 20
<211> LENGTH: 397
<212> TYPE: PRT
<213> ORGANISM: Artificial Sequence
<220> FEATURE:
<223> OTHER INFORMATION: Variant 2 preprotein

<400> SEQUENCE: 20

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
```

-continued

```
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Gly Trp Pro Gln Ser Asp Arg
                325                 330                 335

Asn Pro Arg Tyr Gly Asn His Val Val Leu Leu Leu Lys Met Gln Val
            340                 345                 350

Arg Gly Ala Ala Leu Ala Arg Pro Pro Cys Cys Val Pro Thr Ala Tyr
        355                 360                 365

Ala Gly Lys Leu Leu Ile Ser Leu Ser Glu Glu Arg Ile Ser Ala His
    370                 375                 380

His Val Pro Asn Met Val Ala Thr Glu Cys Gly Cys Arg
385                 390                 395
```

<210> SEQ ID NO 21
<211> LENGTH: 394
<212> TYPE: PRT
<213> ORGANISM: Artificial Sequence
<220> FEATURE:
<223> OTHER INFORMATION: Consensus of Variant 1 and 3 preprotein
<220> FEATURE:
<221> NAME/KEY: VARIANT
<222> LOCATION: 305
<223> OTHER INFORMATION: Xaa is Leu or Phe
<220> FEATURE:
<221> NAME/KEY: VARIANT
<222> LOCATION: 311
<223> OTHER INFORMATION: Xaa is Val or Ile
<220> FEATURE:
<221> NAME/KEY: VARIANT
<222> LOCATION: 312
<223> OTHER INFORMATION: Xaa is Leu or Val
<220> FEATURE:
<221> NAME/KEY: VARIANT
<222> LOCATION: 313
<223> OTHER INFORMATION: Xaa is Ile or Ala
<220> FEATURE:
<221> NAME/KEY: VARIANT
<222> LOCATION: 315
<223> OTHER INFORMATION: Xaa is Glu or Pro
<220> FEATURE:
<221> NAME/KEY: VARIANT
<222> LOCATION: (316)...(316)
<223> OTHER INFORMATION: Xaa is Thr or Gly
<220> FEATURE:

<221> NAME/KEY: VARIANT
<222> LOCATION: (318)...(318)
<223> OTHER INFORMATION: Xaa is Gln or His
<220> FEATURE:
<221> NAME/KEY: VARIANT
<222> LOCATION: (320)...(320)
<223> OTHER INFORMATION: Xaa is Asn or Phe
<220> FEATURE:
<221> NAME/KEY: VARIANT
<222> LOCATION: (321)...(321)
<223> OTHER INFORMATION: Xaa is Asn or Tyr
<220> FEATURE:
<221> NAME/KEY: VARIANT
<222> LOCATION: (323)...(323)
<223> OTHER INFORMATION: Xaa is Gln or His
<220> FEATURE:
<221> NAME/KEY: VARIANT
<222> LOCATION: (325)...(325)
<223> OTHER INFORMATION: Xaa is Val or Glu

<400> SEQUENCE: 21

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300
```

```
Xaa Arg Ala Glu Arg Ser Xaa Xaa Xaa Pro Xaa Xaa Tyr Xaa Ala Xaa
305                 310                 315                 320

Xaa Cys Xaa Gly Xaa Cys Gly Trp Pro Gln Ser Asp Arg Asn Pro Arg
                325                 330                 335

Tyr Gly Asn His Val Val Leu Leu Leu Lys Met Gln Val Arg Gly Ala
            340                 345                 350

Ala Leu Ala Arg Pro Pro Cys Cys Val Pro Thr Ala Tyr Ala Gly Lys
        355                 360                 365

Leu Leu Ile Ser Leu Ser Glu Glu Arg Ile Ser Ala His His Val Pro
    370                 375                 380

Asn Met Val Ala Thr Glu Cys Gly Cys Arg
385                 390


<210> SEQ ID NO 22
<211> LENGTH: 395
<212> TYPE: PRT
<213> ORGANISM: Artificial Sequence
<220> FEATURE:
<223> OTHER INFORMATION: Consensus of Variants 4, 5, 6, 8, 10, and 12
      preprotein
<220> FEATURE:
<221> NAME/KEY: VARIANT
<222> LOCATION: 365
<223> OTHER INFORMATION: Xaa is Ala or Glu
<220> FEATURE:
<221> NAME/KEY: VARIANT
<222> LOCATION: 366
<223> OTHER INFORMATION: Xaa is Tyr or Leu
<220> FEATURE:
<221> NAME/KEY: VARIANT
<222> LOCATION: 389
<223> OTHER INFORMATION: Xaa is Ala or Val
<220> FEATURE:
<221> NAME/KEY: VARIANT
<222> LOCATION: 390
<223> OTHER INFORMATION: Xaa is Thr or Glu
<220> FEATURE:
<221> NAME/KEY: VARIANT
<222> LOCATION: 391
<223> OTHER INFORMATION: Xaa is Glu or Gly

<400> SEQUENCE: 22

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160
```

-continued

```
Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Xaa Xaa Ala Gly
        355                 360                 365

Lys Leu Leu Ile Ser Leu Ser Glu Glu Arg Ile Ser Ala His His Val
    370                 375                 380

Pro Asn Met Val Xaa Xaa Xaa Cys Gly Cys Arg
385                 390                 395
```

<210> SEQ ID NO 23
<211> LENGTH: 392
<212> TYPE: PRT
<213> ORGANISM: Artificial Sequence
<220> FEATURE:
<223> OTHER INFORMATION: Consensus of Variants 7, 9, and 11 preprotein
<220> FEATURE:
<221> NAME/KEY: VARIANT
<222> LOCATION: 305
<223> OTHER INFORMATION: Xaa is Leu of Phe
<220> FEATURE:
<221> NAME/KEY: VARIANT
<222> LOCATION: 311
<223> OTHER INFORMATION: Xaa is Val or Ile
<220> FEATURE:
<221> NAME/KEY: VARIANT
<222> LOCATION: 312
<223> OTHER INFORMATION: Xaa is Leu of Val
<220> FEATURE:
<221> NAME/KEY: VARIANT
<222> LOCATION: 313
<223> OTHER INFORMATION: Xaa is Ile or Ala
<220> FEATURE:
<221> NAME/KEY: VARIANT
<222> LOCATION: 315
<223> OTHER INFORMATION: Xaa is Glu or Pro
<220> FEATURE:
<221> NAME/KEY: VARIANT
<222> LOCATION: (316)...(316)
<223> OTHER INFORMATION: Xaa is Thr or Gly
<220> FEATURE:
<221> NAME/KEY: VARIANT
<222> LOCATION: (318)...(318)

<223> OTHER INFORMATION: Xaa is Gln or His
<220> FEATURE:
<221> NAME/KEY: VARIANT
<222> LOCATION: (320)...(320)
<223> OTHER INFORMATION: Xaa is Asn or Phe
<220> FEATURE:
<221> NAME/KEY: VARIANT
<222> LOCATION: (321)...(321)
<223> OTHER INFORMATION: Xaa is Asn or Tyr
<220> FEATURE:
<221> NAME/KEY: VARIANT
<222> LOCATION: (323)...(323)
<223> OTHER INFORMATION: Xaa is Gln or His
<220> FEATURE:
<221> NAME/KEY: CONFLICT
<222> LOCATION: (325)...(325)
<223> OTHER INFORMATION: Xaa is Val or Glu
<220> FEATURE:
<221> NAME/KEY: VARIANT
<222> LOCATION: (362)...(362)
<223> OTHER INFORMATION: Xaa is Glu or Ala
<220> FEATURE:
<221> NAME/KEY: VARIANT
<222> LOCATION: (363)...(363)
<223> OTHER INFORMATION: Xaa is Leu or Tyr
<220> FEATURE:
<221> NAME/KEY: VARIANT
<222> LOCATION: (386)...(386)
<223> OTHER INFORMATION: Xaa is Val or Ala
<220> FEATURE:
<221> NAME/KEY: VARIANT
<222> LOCATION: (387)...(387)
<223> OTHER INFORMATION: Xaa is Glu or Thr
<220> FEATURE:
<221> NAME/KEY: VARIANT
<222> LOCATION: (388)...(388)
<223> OTHER INFORMATION: Xaa is Gly or Glu

<400> SEQUENCE: 23

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205
```

-continued

```
Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Xaa Arg Ala Glu Arg Ser Xaa Xaa Xaa Pro Xaa Xaa Tyr Xaa Ala Xaa
305                 310                 315                 320

Xaa Cys Xaa Gly Xaa Cys Pro Phe Pro Leu Ala Asp His Leu Asn Ser
                325                 330                 335

Thr Asn His Ala Ile Val Gln Thr Leu Val Asn Ser Val Asn Ser Lys
            340                 345                 350

Ile Pro Lys Ala Cys Cys Val Pro Thr Xaa Xaa Ala Gly Lys Leu Leu
        355                 360                 365

Ile Ser Leu Ser Glu Glu Arg Ile Ser Ala His His Val Pro Asn Met
    370                 375                 380

Val Xaa Xaa Xaa Cys Gly Cys Arg
385                 390
```

<210> SEQ ID NO 24
<211> LENGTH: 394
<212> TYPE: PRT
<213> ORGANISM: Artificial Sequence
<220> FEATURE:
<223> OTHER INFORMATION: Variant 1 preprotein

<400> SEQUENCE: 24

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175
```

```
Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Leu Arg Ala Glu Arg Ser Val Leu Ile Pro Glu Thr Tyr Gln Ala Asn
305                 310                 315                 320

Asn Cys Gln Gly Val Cys Gly Trp Pro Gln Ser Asp Arg Asn Pro Arg
                325                 330                 335

Tyr Gly Asn His Val Val Leu Leu Leu Lys Met Gln Val Arg Gly Ala
            340                 345                 350

Ala Leu Ala Arg Pro Pro Cys Cys Val Pro Thr Ala Tyr Ala Gly Lys
        355                 360                 365

Leu Leu Ile Ser Leu Ser Glu Glu Arg Ile Ser Ala His His Val Pro
    370                 375                 380

Asn Met Val Ala Thr Glu Cys Gly Cys Arg
385                 390


<210> SEQ ID NO 25
<211> LENGTH: 394
<212> TYPE: PRT
<213> ORGANISM: Artificial Sequence
<220> FEATURE:
<223> OTHER INFORMATION: Variant 3 preprotein

<400> SEQUENCE: 25

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140
```

Ile Thr Ser Ala Glu Leu Gln Val Phe Arg Glu Gln Met Gln Asp Ala
145 150 155 160

Leu Gly Asn Asn Ser Ser Phe His His Arg Ile Asn Ile Tyr Glu Ile
165 170 175

Ile Lys Pro Ala Thr Ala Asn Ser Lys Phe Pro Val Thr Arg Leu Leu
180 185 190

Asp Thr Arg Leu Val Asn Gln Asn Ala Ser Arg Trp Glu Ser Phe Asp
195 200 205

Val Thr Pro Ala Val Met Arg Trp Thr Ala Gln Gly His Ala Asn His
210 215 220

Gly Phe Val Val Glu Val Ala His Leu Glu Glu Lys Gln Gly Val Ser
225 230 235 240

Lys Arg His Val Arg Ile Ser Arg Ser Leu His Gln Asp Glu His Ser
245 250 255

Trp Ser Gln Ile Arg Pro Leu Leu Val Thr Phe Gly His Asp Gly Lys
260 265 270

Gly His Pro Leu His Lys Arg Glu Lys Arg Gln Ala Lys His Lys Gln
275 280 285

Arg Lys Arg Leu Lys Ser Ser Cys Lys Arg His Pro Leu Tyr Val Asp
290 295 300

Phe Arg Ala Glu Arg Ser Ile Val Ala Pro Pro Gly Tyr His Ala Phe
305 310 315 320

Tyr Cys His Gly Glu Cys Gly Trp Pro Gln Ser Asp Arg Asn Pro Arg
325 330 335

Tyr Gly Asn His Val Val Leu Leu Leu Lys Met Gln Val Arg Gly Ala
340 345 350

Ala Leu Ala Arg Pro Pro Cys Cys Val Pro Thr Ala Tyr Ala Gly Lys
355 360 365

Leu Leu Ile Ser Leu Ser Glu Glu Arg Ile Ser Ala His His Val Pro
370 375 380

Asn Met Val Ala Thr Glu Cys Gly Cys Arg
385 390

<210> SEQ ID NO 26
<211> LENGTH: 392
<212> TYPE: PRT
<213> ORGANISM: Artificial Sequence
<220> FEATURE:
<223> OTHER INFORMATION: Variant 4 preprotein

<400> SEQUENCE: 26

Met Val Ala Gly Thr Arg Cys Leu Leu Ala Leu Leu Leu Pro Gln Val
1 5 10 15

Leu Leu Gly Gly Ala Ala Gly Leu Val Pro Glu Leu Gly Arg Arg Lys
20 25 30

Phe Ala Ala Ala Ser Ser Gly Arg Pro Ser Ser Gln Pro Ser Asp Glu
35 40 45

Val Leu Ser Glu Phe Glu Leu Arg Leu Leu Ser Met Phe Gly Leu Lys
50 55 60

Gln Arg Pro Thr Pro Ser Arg Asp Ala Val Val Pro Pro Tyr Met Leu
65 70 75 80

Asp Leu Tyr Arg Arg His Ser Gly Gln Pro Gly Ser Pro Ala Pro Asp
85 90 95

His Arg Leu Glu Arg Ala Ala Ser Arg Ala Asn Thr Val Arg Ser Phe
100 105 110

His His Glu Glu Ser Leu Glu Glu Leu Pro Glu Thr Ser Gly Lys Thr
115 120 125

Thr Arg Arg Phe Phe Phe Asn Leu Ser Ser Ile Pro Thr Glu Glu Phe
130 135 140

Ile Thr Ser Ala Glu Leu Gln Val Phe Arg Glu Gln Met Gln Asp Ala
145 150 155 160

Leu Gly Asn Asn Ser Ser Phe His His Arg Ile Asn Ile Tyr Glu Ile
165 170 175

Ile Lys Pro Ala Thr Ala Asn Ser Lys Phe Pro Val Thr Arg Leu Leu
180 185 190

Asp Thr Arg Leu Val Asn Gln Asn Ala Ser Arg Trp Glu Ser Phe Asp
195 200 205

Val Thr Pro Ala Val Met Arg Trp Thr Ala Gln Gly His Ala Asn His
210 215 220

Gly Phe Val Val Glu Val Ala His Leu Glu Glu Lys Gln Gly Val Ser
225 230 235 240

Lys Arg His Val Arg Ile Ser Arg Ser Leu His Gln Asp Glu His Ser
245 250 255

Trp Ser Gln Ile Arg Pro Leu Leu Val Thr Phe Gly His Asp Gly Lys
260 265 270

Gly His Pro Leu His Lys Arg Glu Lys Arg Gln Ala Lys His Lys Gln
275 280 285

Arg Lys Arg Leu Lys Ser Ser Cys Lys Arg His Pro Leu Tyr Val Asp
290 295 300

Leu Arg Ala Glu Arg Ser Val Leu Ile Pro Glu Thr Tyr Gln Ala Asn
305 310 315 320

Asn Cys Gln Gly Val Cys Pro Phe Pro Leu Ala Asp His Leu Asn Ser
325 330 335

Thr Asn His Ala Ile Val Gln Thr Leu Val Asn Ser Val Asn Ser Lys
340 345 350

Ile Pro Lys Ala Cys Cys Val Pro Thr Ala Tyr Ala Gly Lys Leu Leu
355 360 365

Ile Ser Leu Ser Glu Glu Arg Ile Ser Ala His His Val Pro Asn Met
370 375 380

Val Ala Thr Glu Cys Gly Cys Arg
385 390

<210> SEQ ID NO 27
<211> LENGTH: 392
<212> TYPE: PRT
<213> ORGANISM: Artificial Sequence
<220> FEATURE:
<223> OTHER INFORMATION: Variant 5 preprotein

<400> SEQUENCE: 27

Met Val Ala Gly Thr Arg Cys Leu Leu Ala Leu Leu Leu Pro Gln Val
1 5 10 15

Leu Leu Gly Gly Ala Ala Gly Leu Val Pro Glu Leu Gly Arg Arg Lys
20 25 30

Phe Ala Ala Ala Ser Ser Gly Arg Pro Ser Ser Gln Pro Ser Asp Glu
35 40 45

Val Leu Ser Glu Phe Glu Leu Arg Leu Leu Ser Met Phe Gly Leu Lys
50 55 60

Gln Arg Pro Thr Pro Ser Arg Asp Ala Val Val Pro Pro Tyr Met Leu
65 70 75 80

-continued

Asp Leu Tyr Arg Arg His Ser Gly Gln Pro Gly Ser Pro Ala Pro Asp
85 90 95

His Arg Leu Glu Arg Ala Ala Ser Arg Ala Asn Thr Val Arg Ser Phe
100 105 110

His His Glu Glu Ser Leu Glu Glu Leu Pro Glu Thr Ser Gly Lys Thr
115 120 125

Thr Arg Arg Phe Phe Phe Asn Leu Ser Ser Ile Pro Thr Glu Glu Phe
130 135 140

Ile Thr Ser Ala Glu Leu Gln Val Phe Arg Glu Gln Met Gln Asp Ala
145 150 155 160

Leu Gly Asn Asn Ser Ser Phe His His Arg Ile Asn Ile Tyr Glu Ile
165 170 175

Ile Lys Pro Ala Thr Ala Asn Ser Lys Phe Pro Val Thr Arg Leu Leu
180 185 190

Asp Thr Arg Leu Val Asn Gln Asn Ala Ser Arg Trp Glu Ser Phe Asp
195 200 205

Val Thr Pro Ala Val Met Arg Trp Thr Ala Gln Gly His Ala Asn His
210 215 220

Gly Phe Val Val Glu Val Ala His Leu Glu Glu Lys Gln Gly Val Ser
225 230 235 240

Lys Arg His Val Arg Ile Ser Arg Ser Leu His Gln Asp Glu His Ser
245 250 255

Trp Ser Gln Ile Arg Pro Leu Leu Val Thr Phe Gly His Asp Gly Lys
260 265 270

Gly His Pro Leu His Lys Arg Glu Lys Arg Gln Ala Lys His Lys Gln
275 280 285

Arg Lys Arg Leu Lys Ser Ser Cys Lys Arg His Pro Leu Tyr Val Asp
290 295 300

Leu Arg Ala Glu Arg Ser Val Leu Ile Pro Glu Thr Tyr Gln Ala Asn
305 310 315 320

Asn Cys Gln Gly Val Cys Pro Phe Pro Leu Ala Asp His Leu Asn Ser
325 330 335

Thr Asn His Ala Ile Val Gln Thr Leu Val Asn Ser Val Asn Ser Lys
340 345 350

Ile Pro Lys Ala Cys Cys Val Pro Thr Ala Tyr Ala Gly Lys Leu Leu
355 360 365

Ile Ser Leu Ser Glu Glu Arg Ile Ser Ala His His Val Pro Asn Met
370 375 380

Val Val Glu Gly Cys Gly Cys Arg
385 390

<210> SEQ ID NO 28
<211> LENGTH: 392
<212> TYPE: PRT
<213> ORGANISM: Artificial Sequence
<220> FEATURE:
<223> OTHER INFORMATION: Variant 6 preprotein

<400> SEQUENCE: 28

Met Val Ala Gly Thr Arg Cys Leu Leu Ala Leu Leu Leu Pro Gln Val
1 5 10 15

Leu Leu Gly Gly Ala Ala Gly Leu Val Pro Glu Leu Gly Arg Arg Lys
20 25 30

Phe Ala Ala Ala Ser Ser Gly Arg Pro Ser Ser Gln Pro Ser Asp Glu
35 40 45

```
Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Leu Arg Ala Glu Arg Ser Val Leu Ile Pro Glu Thr Tyr Gln Ala Asn
305                 310                 315                 320

Asn Cys Gln Gly Val Cys Pro Phe Pro Leu Ala Asp His Leu Asn Ser
                325                 330                 335

Thr Asn His Ala Ile Val Gln Thr Leu Val Asn Ser Val Asn Ser Lys
            340                 345                 350

Ile Pro Lys Ala Cys Cys Val Pro Thr Glu Leu Ala Gly Lys Leu Leu
        355                 360                 365

Ile Ser Leu Ser Glu Glu Arg Ile Ser Ala His His Val Pro Asn Met
    370                 375                 380

Val Val Glu Gly Cys Gly Cys Arg
385                 390
```

<210> SEQ ID NO 29
<211> LENGTH: 392
<212> TYPE: PRT
<213> ORGANISM: Artificial Sequence
<220> FEATURE:
<223> OTHER INFORMATION: Variant 8 preprotein

<400> SEQUENCE: 29

```
Met Val Ala Gly Thr Arg Cys Leu Leu Ala Leu Leu Leu Pro Gln Val
1               5                   10                  15
```

```
Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Arg Ala Glu Arg Ser Ile Val Ala Pro Pro Gly Tyr His Ala Phe
305                 310                 315                 320

Tyr Cys His Gly Glu Cys Pro Phe Pro Leu Ala Asp His Leu Asn Ser
                325                 330                 335

Thr Asn His Ala Ile Val Gln Thr Leu Val Asn Ser Val Asn Ser Lys
            340                 345                 350

Ile Pro Lys Ala Cys Cys Val Pro Thr Ala Tyr Ala Gly Lys Leu Leu
        355                 360                 365

Ile Ser Leu Ser Glu Glu Arg Ile Ser Ala His His Val Pro Asn Met
    370                 375                 380

Val Ala Thr Glu Cys Gly Cys Arg
385                 390
```

<210> SEQ ID NO 30
<211> LENGTH: 392
<212> TYPE: PRT
<213> ORGANISM: Artificial Sequence
<220> FEATURE:
<223> OTHER INFORMATION: Variant 10 preprotein -continued

<400> SEQUENCE: 30

Met Val Ala Gly Thr Arg Cys Leu Leu Ala Leu Leu Leu Pro Gln Val
1 5 10 15

Leu Leu Gly Gly Ala Ala Gly Leu Val Pro Glu Leu Gly Arg Arg Lys
20 25 30

Phe Ala Ala Ala Ser Ser Gly Arg Pro Ser Ser Gln Pro Ser Asp Glu
35 40 45

Val Leu Ser Glu Phe Glu Leu Arg Leu Leu Ser Met Phe Gly Leu Lys
50 55 60

Gln Arg Pro Thr Pro Ser Arg Asp Ala Val Val Pro Pro Tyr Met Leu
65 70 75 80

Asp Leu Tyr Arg Arg His Ser Gly Gln Pro Gly Ser Pro Ala Pro Asp
85 90 95

His Arg Leu Glu Arg Ala Ala Ser Arg Ala Asn Thr Val Arg Ser Phe
100 105 110

His His Glu Glu Ser Leu Glu Glu Leu Pro Glu Thr Ser Gly Lys Thr
115 120 125

Thr Arg Arg Phe Phe Phe Asn Leu Ser Ser Ile Pro Thr Glu Glu Phe
130 135 140

Ile Thr Ser Ala Glu Leu Gln Val Phe Arg Glu Gln Met Gln Asp Ala
145 150 155 160

Leu Gly Asn Asn Ser Ser Phe His His Arg Ile Asn Ile Tyr Glu Ile
165 170 175

Ile Lys Pro Ala Thr Ala Asn Ser Lys Phe Pro Val Thr Arg Leu Leu
180 185 190

Asp Thr Arg Leu Val Asn Gln Asn Ala Ser Arg Trp Glu Ser Phe Asp
195 200 205

Val Thr Pro Ala Val Met Arg Trp Thr Ala Gln Gly His Ala Asn His
210 215 220

Gly Phe Val Val Glu Val Ala His Leu Glu Glu Lys Gln Gly Val Ser
225 230 235 240

Lys Arg His Val Arg Ile Ser Arg Ser Leu His Gln Asp Glu His Ser
245 250 255

Trp Ser Gln Ile Arg Pro Leu Leu Val Thr Phe Gly His Asp Gly Lys
260 265 270

Gly His Pro Leu His Lys Arg Glu Lys Arg Gln Ala Lys His Lys Gln
275 280 285

Arg Lys Arg Leu Lys Ser Ser Cys Lys Arg His Pro Leu Tyr Val Asp
290 295 300

Phe Arg Ala Glu Arg Ser Ile Val Ala Pro Pro Gly Tyr His Ala Phe
305 310 315 320

Tyr Cys His Gly Glu Cys Pro Phe Pro Leu Ala Asp His Leu Asn Ser
325 330 335

Thr Asn His Ala Ile Val Gln Thr Leu Val Asn Ser Val Asn Ser Lys
340 345 350

Ile Pro Lys Ala Cys Cys Val Pro Thr Ala Tyr Ala Gly Lys Leu Leu
355 360 365

Ile Ser Leu Ser Glu Glu Arg Ile Ser Ala His His Val Pro Asn Met
370 375 380

Val Val Glu Gly Cys Gly Cys Arg
385 390

-continued

<210> SEQ ID NO 31
<211> LENGTH: 392
<212> TYPE: PRT
<213> ORGANISM: Artificial Sequence
<220> FEATURE:
<223> OTHER INFORMATION: Variant 12 preprotein

<400> SEQUENCE: 31

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Arg Ala Glu Arg Ser Ile Val Ala Pro Pro Gly Tyr His Ala Phe
305                 310                 315                 320

Tyr Cys His Gly Glu Cys Pro Phe Pro Leu Ala Asp His Leu Asn Ser
                325                 330                 335

Thr Asn His Ala Ile Val Gln Thr Leu Val Asn Ser Val Asn Ser Lys
            340                 345                 350

Ile Pro Lys Ala Cys Cys Val Pro Thr Glu Leu Ala Gly Lys Leu Leu
        355                 360                 365

Ile Ser Leu Ser Glu Glu Arg Ile Ser Ala His His Val Pro Asn Met
```

```
    370                 375                 380

Val Val Glu Gly Cys Gly Cys Arg
385                 390


<210> SEQ ID NO 32
<211> LENGTH: 395
<212> TYPE: PRT
<213> ORGANISM: Artificial Sequence
<220> FEATURE:
<223> OTHER INFORMATION: Variant 7 preprotein

<400> SEQUENCE: 32

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
```

-continued

```
            340                 345                 350

Asn Ser Lys Ile Pro Lys Ala Cys Cys Val Pro Thr Ala Tyr Ala Gly
        355                 360                 365

Lys Leu Leu Ile Ser Leu Ser Glu Glu Arg Ile Ser Ala His His Val
    370                 375                 380

Pro Asn Met Val Ala Thr Glu Cys Gly Cys Arg
385                 390                 395


<210> SEQ ID NO 33
<211> LENGTH: 395
<212> TYPE: PRT
<213> ORGANISM: Artificial Sequence
<220> FEATURE:
<223> OTHER INFORMATION: Variant 9 preprotein

<400> SEQUENCE: 33

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
```

305 310 315 320

His Ala Phe Tyr Cys His Gly Glu Cys Pro Phe Pro Leu Ala Asp His
325 330 335

Leu Asn Ser Thr Asn His Ala Ile Val Gln Thr Leu Val Asn Ser Val
340 345 350

Asn Ser Lys Ile Pro Lys Ala Cys Cys Val Pro Thr Ala Tyr Ala Gly
355 360 365

Lys Leu Leu Ile Ser Leu Ser Glu Glu Arg Ile Ser Ala His His Val
370 375 380

Pro Asn Met Val Val Glu Gly Cys Gly Cys Arg
385 390 395

<210> SEQ ID NO 34
<211> LENGTH: 395
<212> TYPE: PRT
<213> ORGANISM: Artificial Sequence
<220> FEATURE:
<223> OTHER INFORMATION: Variant 11 preprotein

<400> SEQUENCE: 34

Met Val Ala Gly Thr Arg Cys Leu Leu Ala Leu Leu Leu Pro Gln Val
1 5 10 15

Leu Leu Gly Gly Ala Ala Gly Leu Val Pro Glu Leu Gly Arg Arg Lys
20 25 30

Phe Ala Ala Ala Ser Ser Gly Arg Pro Ser Ser Gln Pro Ser Asp Glu
35 40 45

Val Leu Ser Glu Phe Glu Leu Arg Leu Leu Ser Met Phe Gly Leu Lys
50 55 60

Gln Arg Pro Thr Pro Ser Arg Asp Ala Val Val Pro Pro Tyr Met Leu
65 70 75 80

Asp Leu Tyr Arg Arg His Ser Gly Gln Pro Gly Ser Pro Ala Pro Asp
85 90 95

His Arg Leu Glu Arg Ala Ala Ser Arg Ala Asn Thr Val Arg Ser Phe
100 105 110

His His Glu Glu Ser Leu Glu Glu Leu Pro Glu Thr Ser Gly Lys Thr
115 120 125

Thr Arg Arg Phe Phe Phe Asn Leu Ser Ser Ile Pro Thr Glu Glu Phe
130 135 140

Ile Thr Ser Ala Glu Leu Gln Val Phe Arg Glu Gln Met Gln Asp Ala
145 150 155 160

Leu Gly Asn Asn Ser Ser Phe His His Arg Ile Asn Ile Tyr Glu Ile
165 170 175

Ile Lys Pro Ala Thr Ala Asn Ser Lys Phe Pro Val Thr Arg Leu Leu
180 185 190

Asp Thr Arg Leu Val Asn Gln Asn Ala Ser Arg Trp Glu Ser Phe Asp
195 200 205

Val Thr Pro Ala Val Met Arg Trp Thr Ala Gln Gly His Ala Asn His
210 215 220

Gly Phe Val Val Glu Val Ala His Leu Glu Glu Lys Gln Gly Val Ser
225 230 235 240

Lys Arg His Val Arg Ile Ser Arg Ser Leu His Gln Asp Glu His Ser
245 250 255

Trp Ser Gln Ile Arg Pro Leu Leu Val Thr Phe Gly His Asp Gly Lys
260 265 270

Gly His Pro Leu His Lys Arg Glu Lys Arg Gln Ala Lys His Lys Gln

-continued

```
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ala Gly
        355                 360                 365

Lys Leu Leu Ile Ser Leu Ser Glu Glu Arg Ile Ser Ala His His Val
    370                 375                 380

Pro Asn Met Val Val Glu Gly Cys Gly Cys Arg
385                 390                 395


<210> SEQ ID NO 35
<211> LENGTH: 336
<212> TYPE: DNA
<213> ORGANISM: Artificial Sequence
<220> FEATURE:
<223> OTHER INFORMATION: Variant 1 mature gene
<220> FEATURE:
<221> NAME/KEY: misc_feature
<222> LOCATION: (0)...(0)
<223> OTHER INFORMATION: n = a, c, t, or g

<400> SEQUENCE: 35

cargcnaarc ayaarcarmg naarmgnytn aarwsnwsnt gyaarmgnca yccnytntay     60

gtngayytnm gngcngarmg nwsngtnytn athccngara cntaycargc naayaaytgy    120

carggngtnt gyggntggcc ncarwsngay mgnaayccnm gntayggnaa ycaygtngtn    180

ytnytnytna aratgcargt nmgnggngcn gcnytngcnm gnccnccntg ytgygtnccn    240

acngcntayg cnggnaaryt nytnathwsn ytnwsngarg armgnathws ngcncaycay    300

gtnccnaaya tggtngcnac ngartgyggn tgymgn                              336


<210> SEQ ID NO 36
<211> LENGTH: 345
<212> TYPE: DNA
<213> ORGANISM: Artificial Sequence
<220> FEATURE:
<223> OTHER INFORMATION: Variant 2 mature gene
<220> FEATURE:
<221> NAME/KEY: misc_feature
<222> LOCATION: (0)...(0)
<223> OTHER INFORMATION: n = a, c, t, or g

<400> SEQUENCE: 36

cargcnaarc ayaarcarmg naarmgnytn aarwsnwsnt gyaarmgnca yccnytntay     60

gtngayttyw sngaygtngg ntggaaygay tggathgtng cnccnccngg ntaycaygcn    120

ttytaytgyc ayggngartg yggntggccn carwsngaym gnaayccnmg ntayggnaay    180

caygtngtny tnytnytnaa ratgcargtn mgnggngcng cnytngcnmg nccnccntgy    240

tgygtnccna cngcntaygc nggnaarytn ytnathwsny tnwsngarga rmgnathwsn    300

gcncaycayg tnccnaayat ggtngcnacn gartgyggnt gymgn                    345


<210> SEQ ID NO 37
<211> LENGTH: 336
<212> TYPE: DNA
```

<213> ORGANISM: Artificial Sequence
<220> FEATURE:
<223> OTHER INFORMATION: Variant 3 mature gene
<220> FEATURE:
<221> NAME/KEY: misc_feature
<222> LOCATION: (0)...(0)
<223> OTHER INFORMATION: n = a, c, t, or g

<400> SEQUENCE: 37
cargcnaarc ayaarcarmg naarmgnytn aarwsnwsnt gyaarmgnca yccnytntay 60
gtngayttym gngcngarmg nwsnathgtn gcnccnccng gntaycaygc nttytaytgy 120
cayggngart gyggntggcc ncarwsngay mgnaayccnm gntayggnaa ycaygtngtn 180
ytnytnytna aratgcargt nmgnggngcn gcnytngcnm gnccnccntg ytgygtnccn 240
acngcntayg cnggnaaryt nytnathwsn ytnwsngarg armgnathws ngcncaycay 300
gtnccnaaya tggtngcnac ngartgyggn tgymgn 336

<210> SEQ ID NO 38
<211> LENGTH: 330
<212> TYPE: DNA
<213> ORGANISM: Artificial Sequence
<220> FEATURE:
<223> OTHER INFORMATION: Variant 4 mature gene
<220> FEATURE:
<221> NAME/KEY: misc_feature
<222> LOCATION: (0)...(0)
<223> OTHER INFORMATION: n = a, c, t, or g

<400> SEQUENCE: 38
cargcnaarc ayaarcarmg naarmgnytn aarwsnwsnt gyaarmgnca yccnytntay 60
gtngayytnm gngcngarmg nwsngtnytn athccngara cntaycargc naayaaytgy 120
carggngtnt gyccnttycc nytngcngay cayytnaayw snacnaayca ygcnathgtn 180
caracnytng tnaaywsngt naaywsnaar athccnaarg cntgytgygt nccnacngcn 240
taygcnggna arytnytnat hwsnytnwsn gargarmgna thwsngcnca ycaygtnccn 300
aayatggtng cnacngartg yggntgymgn 330

<210> SEQ ID NO 39
<211> LENGTH: 330
<212> TYPE: DNA
<213> ORGANISM: Artificial Sequence
<220> FEATURE:
<223> OTHER INFORMATION: Variant 5 mature gene
<220> FEATURE:
<221> NAME/KEY: misc_feature
<222> LOCATION: (0)...(0)
<223> OTHER INFORMATION: n = a, c, t, or g

<400> SEQUENCE: 39
cargcnaarc ayaarcarmg naarmgnytn aarwsnwsnt gyaarmgnca yccnytntay 60
gtngayytnm gngcngarmg nwsngtnytn athccngara cntaycargc naayaaytgy 120
carggngtnt gyccnttycc nytngcngay cayytnaayw snacnaayca ygcnathgtn 180
caracnytng tnaaywsngt naaywsnaar athccnaarg cntgytgygt nccnacngcn 240
taygcnggna arytnytnat hwsnytnwsn gargarmgna thwsngcnca ycaygtnccn 300
aayatggtng tngarggntg yggntgymgn 330

<210> SEQ ID NO 40
<211> LENGTH: 330
<212> TYPE: DNA
<213> ORGANISM: Artificial Sequence
<220> FEATURE:
<223> OTHER INFORMATION: Variant 6 mature gene
<220> FEATURE:
<221> NAME/KEY: misc_feature
<222> LOCATION: (0)...(0)
<223> OTHER INFORMATION: n = a, c, t, or g

<400> SEQUENCE: 40

```
cargcnaarc ayaarcarmg naarmgnytn aarwsnwsnt gyaarmgnca yccnytntay     60

gtngayytnm gngcngarmg nwsngtnytn athccngara cntaycargc naayaaytgy    120

carggngtnt gyccnttycc nytngcngay cayytnaayw snacnaayca ygcnathgtn    180

caracnytng tnaaywsngt naaywsnaar athccnaarg cntgytgygt nccnacngar    240

ytngcnggna arytnytnat hwsnytnwsn gargarmgna thwsngcnca ycaygtnccn    300

aayatggtng tngarggntg yggntgymgn                                     330
```

<210> SEQ ID NO 41
<211> LENGTH: 339
<212> TYPE: DNA
<213> ORGANISM: Artificial Sequence
<220> FEATURE:
<223> OTHER INFORMATION: Variant 7 mature gene
<220> FEATURE:
<221> NAME/KEY: misc_feature
<222> LOCATION: (0)...(0)
<223> OTHER INFORMATION: n = a, c, t, or g

<400> SEQUENCE: 41

```
cargcnaarc ayaarcarmg naarmgnytn aarwsnwsnt gyaarmgnca yccnytntay     60

gtngayttyw sngaygtngg ntggaaygay tggathgtng cnccnccngg ntaycaygcn    120

ttytaytgyc ayggngartg yccnttyccn ytngcngayc ayytnaayws nacnaaycay    180

gcnathgtnc aracnytngt naaywsngtn aaywsnaara thccnaargc ntgytgygtn    240

ccnacngcnt aygcnggnaa rytnytnath wsnytnwsng argarmgnat hwsngcncay    300

caygtnccna ayatggtngc nacngartgy ggntgymgn                           339
```

<210> SEQ ID NO 42
<211> LENGTH: 330
<212> TYPE: DNA
<213> ORGANISM: Artificial Sequence
<220> FEATURE:
<223> OTHER INFORMATION: Variant 8 mature gene
<220> FEATURE:
<221> NAME/KEY: misc_feature
<222> LOCATION: (0)...(0)
<223> OTHER INFORMATION: n = a, c, t, or g

<400> SEQUENCE: 42

```
cargcnaarc ayaarcarmg naarmgnytn aarwsnwsnt gyaarmgnca yccnytntay     60

gtngayttym gngcngarmg nwsnathgtn gcnccnccng gntaycaygc nttytaytgy    120

cayggngart gyccnttycc nytngcngay cayytnaayw snacnaayca ygcnathgtn    180

caracnytng tnaaywsngt naaywsnaar athccnaarg cntgytgygt nccnacngcn    240

taygcnggna arytnytnat hwsnytnwsn gargarmgna thwsngcnca ycaygtnccn    300

aayatggtng cnacngartg yggntgymgn                                     330
```

<210> SEQ ID NO 43
<211> LENGTH: 339
<212> TYPE: DNA
<213> ORGANISM: Artificial Sequence
<220> FEATURE:

<223> OTHER INFORMATION: Variant 9 mature gene
<220> FEATURE:
<221> NAME/KEY: misc_feature
<222> LOCATION: (0)...(0)
<223> OTHER INFORMATION: n = a, c, t, or g

<400> SEQUENCE: 43
cargcnaarc ayaarcarmg naarmgnytn aarwsnwsnt gyaarmgnca yccnytntay 60
gtngayttyw sngaygtngg ntggaaygay tggathgtng cnccnccngg ntaycaygcn 120
ttytaytgyc ayggngartg yccnttyccn ytngcngayc ayytnaayws nacnaaycay 180
gcnathgtnc aracnytngt naaywsngtn aaywsnaara thccnaargc ntgytgygtn 240
ccnacngcnt aygcnggnaa rytnytnath wsnytnwsng argarmgnat hwsngcncay 300
caygtnccna ayatggtngt ngarggntgy ggntgymgn 339

<210> SEQ ID NO 44
<211> LENGTH: 330
<212> TYPE: DNA
<213> ORGANISM: Artificial Sequence
<220> FEATURE:
<223> OTHER INFORMATION: Variant 10 mature gene
<220> FEATURE:
<221> NAME/KEY: misc_feature
<222> LOCATION: (0)...(0)
<223> OTHER INFORMATION: n = a, c, t, or g

<400> SEQUENCE: 44
cargcnaarc ayaarcarmg naarmgnytn aarwsnwsnt gyaarmgnca yccnytntay 60
gtngayttym gngcngarmg nwsnathgtn gcnccnccng gntaycaygc nttytaytgy 120
cayggngart gyccnttycc nytngcngay cayytnaayw snacnaayca ygcnathgtn 180
caracnytng tnaaywsngt naaywsnaar athccnaarg cntgytgygt nccnacngcn 240
taygcnggna arytnytnat hwsnytnwsn gargarmgna thwsngcnca ycaygtnccn 300
aayatggtng tngarggntg yggntgymgn 330

<210> SEQ ID NO 45
<211> LENGTH: 339
<212> TYPE: DNA
<213> ORGANISM: Artificial Sequence
<220> FEATURE:
<223> OTHER INFORMATION: Variant 11 mature gene
<220> FEATURE:
<221> NAME/KEY: misc_feature
<222> LOCATION: (0)...(0)
<223> OTHER INFORMATION: n = a, c, t, or g

<400> SEQUENCE: 45
cargcnaarc ayaarcarmg naarmgnytn aarwsnwsnt gyaarmgnca yccnytntay 60
gtngayttyw sngaygtngg ntggaaygay tggathgtng cnccnccngg ntaycaygcn 120
ttytaytgyc ayggngartg yccnttyccn ytngcngayc ayytnaayws nacnaaycay 180
gcnathgtnc aracnytngt naaywsngtn aaywsnaara thccnaargc ntgytgygtn 240
ccnacngary tngcnggnaa rytnytnath wsnytnwsng argarmgnat hwsngcncay 300
caygtnccna ayatggtngt ngarggntgy ggntgymgn 339

<210> SEQ ID NO 46
<211> LENGTH: 330
<212> TYPE: DNA
<213> ORGANISM: Artificial Sequence
<220> FEATURE:
<223> OTHER INFORMATION: Variant 12 mature gene
<220> FEATURE:
<221> NAME/KEY: misc_feature
<222> LOCATION: (0)...(0)
<223> OTHER INFORMATION: n = a, c, t, or g

<400> SEQUENCE: 46

```
cargcnaarc ayaarcarmg naarmgnytn aarwsnwsnt gyaarmgnca yccnytntay     60

gtngayttym gngcngarmg nwsnathgtn gcnccnccng gntaycaygc nttytaytgy    120

cayggngart gyccnttycc nytngcngay cayytnaayw snacnaayca ygcnathgtn    180

caracnytng tnaaywsngt naaywsnaar athccnaarg cntgytgygt nccnacngar    240

ytngcnggna arytnytnat hwsnytnwsn gargarmgna thwsngcnca ycaygtnccn    300

aayatggtng tngarggntg yggntgymgn                                     330
```

<210> SEQ ID NO 47
<211> LENGTH: 1182
<212> TYPE: DNA
<213> ORGANISM: Artificial Sequence
<220> FEATURE:
<223> OTHER INFORMATION: Variant 1 preprotein gene
<220> FEATURE:
<221> NAME/KEY: misc_feature
<222> LOCATION: (0)...(0)
<223> OTHER INFORMATION: n = a, c, t, or g

<400> SEQUENCE: 47

```
atggtngcng gnacnmgntg yytnytngcn ytnytnytnc cncargtnyt nytnggnggn     60

gcngcnggny tngtnccnga rytnggnmgn mgnaarttyg cngcngcnws nwsnggnmgn    120

ccnwsnwsnc arccnwsnga ygargtnytn wsngarttyg arytnmgnyt nytnwsnatg    180

ttyggnytna arcarmgncc nacnccnwsn mgngaygcng tngtnccncc ntayatgytn    240

gayytntaym gnmgncayws nggncarccn ggnwsnccng cnccngayca ymgnytngar    300

mgngcngcnw snmgngcnaa yacngtnmgn wsnttycayc aygargarws nytngargar    360

ytnccngara cnwsnggnaa racnacnmgn mgnttyttyt tyaayytnws nwsnathccn    420

acngargart tyathacnws ngcngarytn cargtnttym gngarcarat gcargaygcn    480

ytnggnaaya aywsnwsntt ycaycaymgn athaayatht aygarathat haarccngcn    540

acngcnaayw snaarttycc ngtnacnmgn ytnytngaya cnmgnytngt naaycaraay    600

gcnwsnmgnt gggarwsntt ygaygtnacn ccngcngtna tgmgntggac ngcncarggn    660

caygcnaayc ayggnttygt ngtngargtn gcncayytng argaraarca rggngtnwsn    720

aarmgncayg tnmgnathws nmgnwsnytn caycargayg arcaywsntg gwsncarath    780

mgnccnytny tngtnacntt yggncaygay ggnaarggnc ayccnytnca yaarmgngar    840

aarmgncarg cnaarcayaa rcarmgnaar mgnytnaarw snwsntgyaa rmgncayccn    900

ytntaygtng ayytnmgngc ngarmgnwsn gtnytnathc cngaracnta ycargcnaay    960

aaytgycarg gngtntgygg ntggccncar wsngaymgna ayccnmgnta yggnaaycay   1020

gtngtnytny tnytnaarat gcargtnmgn ggngcngcny tngcnmgncc nccntgytgy   1080

gtnccnacng cntaygcngg naarytnytn athwsnytnw sngargarmg nathwsngcn   1140

caycaygtnc cnaayatggt ngcnacngar tgyggntgym gn                      1182
```

<210> SEQ ID NO 48
<211> LENGTH: 1191
<212> TYPE: DNA
<213> ORGANISM: Artificial Sequence
<220> FEATURE:

```
<223> OTHER INFORMATION: Variant 2 preprotein gene
<220> FEATURE:
<221> NAME/KEY: misc_feature
<222> LOCATION: (0)...(0)
<223> OTHER INFORMATION: n = a, c, t, or g

<400> SEQUENCE: 48

atggtngcng gnacnmgntg yytnytngcn ytnytnytnc cncargtnyt nytnggnggn     60

gcngcnggny tngtnccnga rytnggnmgn mgnaarttyg cngcngcnws nwsnggnmgn    120

ccnwsnwsnc arccnwsnga ygargtnytn wsngarttyg arytnmgnyt nytnwsnatg    180

ttyggnytna arcarmgncc nacnccnwsn mgngaygcng tngtnccncc ntayatgytn    240

gayytntaym gnmgncayws nggncarccn ggnwsnccng cnccngayca ymgnytngar    300

mgngcngcnw snmgngcnaa yacngtnmgn wsnttycayc aygargarws nytngargar    360

ytnccngara cnwsnggnaa racnacnmgn mgnttyttyt tyaayytnws nwsnathccn    420

acngargart tyathacnws ngcngarytn cargtnttym gngarcarat gcargaygcn    480

ytnggnaaya aywsnwsntt ycaycaymgn athaayatht aygarathat haarccngcn    540

acngcnaayw snaarttycc ngtnacnmgn ytnytngaya cnmgnytngt naaycaraay    600

gcnwsnmgnt gggarwsntt ygaygtnacn ccngcngtna tgmgntggac ngcncarggn    660

caygcnaayc ayggnttygt ngtngargtn gcncayytng argaraarca rggngtnwsn    720

aarmgncayg tnmgnathws nmgnwsnytn caycargayg arcaywsntg gwsncarath    780

mgnccnytny tngtnacntt yggncaygay ggnaarggnc ayccnytnca yaarmgngar    840

aarmgncarg cnaarcayaa rcarmgnaar mgnytnaarw snwsntgyaa rmgncayccn    900

ytntaygtng ayttywsnga ygtnggntgg aaygaytgga thgtngcncc nccnggntay    960

caygcnttyt aytgycaygg ngartgyggn tggccncarw sngaymgnaa yccnmgntay   1020

ggnaaycayg tngtnytnyt nytnaaratg cargtnmgng gngcngcnyt ngcnmgnccn   1080

ccntgytgyg tnccnacngc ntaygcnggn aarytnytna thwsnytnws ngargarmgn   1140

athwsngcnc aycaygtncc naayatggtn gcnacngart gyggntgymg n            1191


<210> SEQ ID NO 49
<211> LENGTH: 1182
<212> TYPE: DNA
<213> ORGANISM: Artificial Sequence
<220> FEATURE:
<223> OTHER INFORMATION: Variant 3 preprotein gene
<220> FEATURE:
<221> NAME/KEY: misc_feature
<222> LOCATION: (0)...(0)
<223> OTHER INFORMATION: n = a, c, t, or g

<400> SEQUENCE: 49

atggtngcng gnacnmgntg yytnytngcn ytnytnytnc cncargtnyt nytnggnggn     60

gcngcnggny tngtnccnga rytnggnmgn mgnaarttyg cngcngcnws nwsnggnmgn    120

ccnwsnwsnc arccnwsnga ygargtnytn wsngarttyg arytnmgnyt nytnwsnatg    180

ttyggnytna arcarmgncc nacnccnwsn mgngaygcng tngtnccncc ntayatgytn    240

gayytntaym gnmgncayws nggncarccn ggnwsnccng cnccngayca ymgnytngar    300

mgngcngcnw snmgngcnaa yacngtnmgn wsnttycayc aygargarws nytngargar    360

ytnccngara cnwsnggnaa racnacnmgn mgnttyttyt tyaayytnws nwsnathccn    420

acngargart tyathacnws ngcngarytn cargtnttym gngarcarat gcargaygcn    480

ytnggnaaya aywsnwsntt ycaycaymgn athaayatht aygarathat haarccngcn    540
```

acngcnaayw snaarttycc ngtnacnmgn ytnytngaya cnmgnytngt naaycaraay 600
gcnwsnmgnt gggarwsntt ygaygtnacn ccngcngtna tgmgntggac ngcncarggn 660
caygcnaayc ayggnttygt ngtngargtn gcncayytng argaraarca rggngtnwsn 720
aarmgncayg tnmgnathws nmgnwsnytn caycargayg arcaywsntg gwsncarath 780
mgnccnytny tngtnacntt yggncaygay ggnaarggnc ayccnytnca yaarmgngar 840
aarmgncarg cnaarcayaa rcarmgnaar mgnytnaarw snwsntgyaa rmgncayccn 900
ytntaygtng ayttymgngc ngarmgnwsn athgtngcnc cnccnggnta ycaygcntty 960
taytgycayg gngartgygg ntggccncar wsngaymgna ayccnmgnta yggnaaycay 1020
gtngtnytny tnytnaarat gcargtnmgn ggngcngcny tngcnmgncc nccntgytgy 1080
gtnccnacng cntaygcngg naarytnytn athwsnytnw sngargarmg nathwsngcn 1140
caycaygtnc cnaayatggt ngcnacngar tgyggntgym gn 1182

<210> SEQ ID NO 50
<211> LENGTH: 1176
<212> TYPE: DNA
<213> ORGANISM: Artificial Sequence
<220> FEATURE:
<223> OTHER INFORMATION: Variant 4 preprotein gene
<220> FEATURE:
<221> NAME/KEY: misc_feature
<222> LOCATION: (0)...(0)
<223> OTHER INFORMATION: n = a, c, t, or g

<400> SEQUENCE: 50
atggtngcng gnacnmgntg yytnytngcn ytnytnytnc cncargtnyt nytnggnggn 60
gcngcnggny tngtnccnga rytnggnmgn mgnaarttyg cngcngcnws nwsnggnmgn 120
ccnwsnwsnc arccnwsnga ygargtnytn wsngarttyg arytnmgnyt nytnwsnatg 180
ttyggnytna arcarmgncc nacnccnwsn mgngaygcng tngtnccncc ntayatgytn 240
gayytntaym gnmgncayws nggncarccn ggnwsnccng cnccngayca ymgnytngar 300
mgngcngcnw snmgngcnaa yacngtnmgn wsnttycayc aygargarws nytngargar 360
ytnccngara cnwsnggnaa racnacnmgn mgnttyttyt tyaayytnws nwsnathccn 420
acngargart tyathacnws ngcngarytn cargtnttym gngarcarat gcargaygcn 480
ytnggnaaya aywsnwsntt ycaycaymgn athaayatht aygarathat haarccngcn 540
acngcnaayw snaarttycc ngtnacnmgn ytnytngaya cnmgnytngt naaycaraay 600
gcnwsnmgnt gggarwsntt ygaygtnacn ccngcngtna tgmgntggac ngcncarggn 660
caygcnaayc ayggnttygt ngtngargtn gcncayytng argaraarca rggngtnwsn 720
aarmgncayg tnmgnathws nmgnwsnytn caycargayg arcaywsntg gwsncarath 780
mgnccnytny tngtnacntt yggncaygay ggnaarggnc ayccnytnca yaarmgngar 840
aarmgncarg cnaarcayaa rcarmgnaar mgnytnaarw snwsntgyaa rmgncayccn 900
ytntaygtng ayytnmgngc ngarmgnwsn gtnytnathc cngaracnta ycargcnaay 960
aaytgycarg gngtntgycc nttyccnytn gcngaycayy tnaaywsnac naaycaygcn 1020
athgtncara cnytngtnaa ywsngtnaay wsnaarathc cnaargcntg ytgygtnccn 1080
acngcntayg cnggnaaryt nytnathwsn ytnwsngarg armgnathws ngcncaycay 1140
gtnccnaaya tggtngcnac ngartgyggn tgymgn 1176

<210> SEQ ID NO 51

<211> LENGTH: 1176
<212> TYPE: DNA
<213> ORGANISM: Artificial Sequence
<220> FEATURE:
<223> OTHER INFORMATION: Variant 5 preprotein gene
<220> FEATURE:
<221> NAME/KEY: misc_feature
<222> LOCATION: (0)...(0)
<223> OTHER INFORMATION: n = a, c, t, or g

<400> SEQUENCE: 51
atggtngcng gnacnmgntg yytnytngcn ytnytnytnc cncargtnyt nytnggnggn 60
gcngcnggny tngtnccnga rytnggnmgn mgnaarttyg cngcngcnws nwsnggnmgn 120
ccnwsnwsnc arccnwsnga ygargtnytn wsngarttyg arytnmgnyt nytnwsnatg 180
ttyggnytna arcarmgncc nacnccnwsn mgngaygcng tngtnccncc ntayatgytn 240
gayytntaym gnmgncayws nggncarccn ggnwsnccng cnccngayca ymgnytngar 300
mgngcngcnw snmgngcnaa yacngtnmgn wsnttycayc aygargarws nytngargar 360
ytnccngara cnwsnggnaa racnacnmgn mgnttyttyt tyaayytnws nwsnathccn 420
acngargart tyathacnws ngcngarytn cargtnttym gngarcarat gcargaygcn 480
ytnggnaaya aywsnwsntt ycaycaymgn athaayatht aygarathat haarccngcn 540
acngcnaayw snaarttycc ngtnacnmgn ytnytngaya cnmgnytngt naaycaraay 600
gcnwsnmgnt gggarwsntt ygaygtnacn ccngcngtna tgmgntggac ngcncarggn 660
caygcnaayc ayggnttygt ngtngargtn gcncayytng argaraarca rggngtnwsn 720
aarmgncayg tnmgnathws nmgnwsnytn caycargayg arcaywsntg gwsncarath 780
mgnccnytny tngtnacntt yggncaygay ggnaarggnc ayccnytnca yaarmgngar 840
aarmgncarg cnaarcayaa rcarmgnaar mgnytnaarw snwsntgyaa rmgncayccn 900
ytntaygtng ayytnmgngc ngarmgnwsn gtnytnathc cngaracnta ycargcnaay 960
aaytgycarg gngtntgycc nttyccnytn gcngaycayy tnaaywsnac naaycaygcn 1020
athgtncara cnytngtnaa ywsngtnaay wsnaarathc cnaargcntg ytgygtnccn 1080
acngcntayg cnggnaaryt nytnathwsn ytnwsngarg armgnathws ngcncaycay 1140
gtnccnaaya tggtngtnga rggntgyggn tgymgn 1176

<210> SEQ ID NO 52
<211> LENGTH: 1176
<212> TYPE: DNA
<213> ORGANISM: Artificial Sequence
<220> FEATURE:
<223> OTHER INFORMATION: Variant 6 preprotein gene
<220> FEATURE:
<221> NAME/KEY: misc_feature
<222> LOCATION: (0)...(0)
<223> OTHER INFORMATION: n = a, c, t, or g

<400> SEQUENCE: 52
atggtngcng gnacnmgntg yytnytngcn ytnytnytnc cncargtnyt nytnggnggn 60
gcngcnggny tngtnccnga rytnggnmgn mgnaarttyg cngcngcnws nwsnggnmgn 120
ccnwsnwsnc arccnwsnga ygargtnytn wsngarttyg arytnmgnyt nytnwsnatg 180
ttyggnytna arcarmgncc nacnccnwsn mgngaygcng tngtnccncc ntayatgytn 240
gayytntaym gnmgncayws nggncarccn ggnwsnccng cnccngayca ymgnytngar 300
mgngcngcnw snmgngcnaa yacngtnmgn wsnttycayc aygargarws nytngargar 360
ytnccngara cnwsnggnaa racnacnmgn mgnttyttyt tyaayytnws nwsnathccn 420
acngargart tyathacnws ngcngarytn cargtnttym gngarcarat gcargaygcn 480
ytnggnaaya aywsnwsntt ycaycaymgn athaayatht aygarathat haarccngcn 540
acngcnaayw snaarttycc ngtnacnmgn ytnytngaya cnmgnytngt naaycaraay 600
gcnwsnmgnt gggarwsntt ygaygtnacn ccngcngtna tgmgntggac ngcncarggn 660
caygcnaayc ayggnttygt ngtngargtn gcncayytng argaraarca rggngtnwsn 720
aarmgncayg tnmgnathws nmgnwsnytn caycargayg arcaywsntg gwsncarath 780
mgnccnytny tngtnacntt yggncaygay ggnaarggnc ayccnytnca yaarmgngar 840
aarmgncarg cnaarcayaa rcarmgnaar mgnytnaarw snwsntgyaa rmgncayccn 900
ytntaygtng ayytnmgngc ngarmgnwsn gtnytnathc cngaracnta ycargcnaay 960
aaytgycarg gngtntgycc nttyccnytn gcngaycayy tnaaywsnac naaycaygcn 1020
athgtncara cnytngtnaa ywsngtnaay wsnaarathc cnaargcntg ytgygtnccn 1080
acngarytng cnggnaaryt nytnathwsn ytnwsngarg armgnathws ngcncaycay 1140
gtnccnaaya tggtngtnga rggntgyggn tgymgn 1176

<210> SEQ ID NO 53
<211> LENGTH: 1185
<212> TYPE: DNA
<213> ORGANISM: Artificial Sequence
<220> FEATURE:
<223> OTHER INFORMATION: Variant 7 preprotein gene
<220> FEATURE:
<221> NAME/KEY: misc_feature
<222> LOCATION: (0)...(0)
<223> OTHER INFORMATION: n = a, c, t, or g

<400> SEQUENCE: 53
atggtngcng gnacnmgntg yytnytngcn ytnytnytnc cncargtnyt nytnggnggn 60
gcngcnggny tngtnccnga rytnggnmgn mgnaarttyg cngcngcnws nwsnggnmgn 120
ccnwsnwsnc arccnwsnga ygargtnytn wsngarttyg arytnmgnyt nytnwsnatg 180
ttyggnytna arcarmgncc nacnccnwsn mgngaygcng tngtnccncc ntayatgytn 240
gayytntaym gnmgncayws nggncarccn ggnwsnccng cnccngayca ymgnytngar 300
mgngcngcnw snmgngcnaa yacngtnmgn wsnttycayc aygargarws nytngargar 360
ytnccngara cnwsnggnaa racnacnmgn mgnttyttyt tyaayytnws nwsnathccn 420
acngargart tyathacnws ngcngarytn cargtnttym gngarcarat gcargaygcn 480
ytnggnaaya aywsnwsntt ycaycaymgn athaayatht aygarathat haarccngcn 540
acngcnaayw snaarttycc ngtnacnmgn ytnytngaya cnmgnytngt naaycaraay 600
gcnwsnmgnt gggarwsntt ygaygtnacn ccngcngtna tgmgntggac ngcncarggn 660
caygcnaayc ayggnttygt ngtngargtn gcncayytng argaraarca rggngtnwsn 720
aarmgncayg tnmgnathws nmgnwsnytn caycargayg arcaywsntg gwsncarath 780
mgnccnytny tngtnacntt yggncaygay ggnaarggnc ayccnytnca yaarmgngar 840
aarmgncarg cnaarcayaa rcarmgnaar mgnytnaarw snwsntgyaa rmgncayccn 900
ytntaygtng ayttywsnga ygtnggntgg aaygaytgga thgtngcncc nccnggntay 960
caygcnttyt aytgycaygg ngartgyccn ttyccnytng cngaycayyt naaywsnacn 1020
aaycaygcna thgtncarac nytngtnaay wsngtnaayw snaarathcc naargcntgy 1080
tgygtnccna cngcntaygc nggnaarytn ytnathwsny tnwsngarga rmgnathwsn 1140
gcncaycayg tnccnaayat ggtngcnacn gartgyggnt gymgn 1185

<210> SEQ ID NO 54
<211> LENGTH: 1176
<212> TYPE: DNA
<213> ORGANISM: Artificial Sequence
<220> FEATURE:
<223> OTHER INFORMATION: Variant 8 preprotein gene
<220> FEATURE:
<221> NAME/KEY: misc_feature
<222> LOCATION: (0)...(0)
<223> OTHER INFORMATION: n = a, c, t, or g

<400> SEQUENCE: 54
atggtngcng gnacnmgntg yytnytngcn ytnytnytnc cncargtnyt nytnggnggn 60
gcngcnggny tngtnccnga rytnggnmgn mgnaarttyg cngcngcnws nwsnggnmgn 120
ccnwsnwsnc arccnwsnga ygargtnytn wsngarttyg arytnmgnyt nytnwsnatg 180
ttyggnytna arcarmgncc nacnccnwsn mgngaygcng tngtnccncc ntayatgytn 240
gayytntaym gnmgncayws nggncarccn ggnwsnccng cnccngayca ymgnytngar 300
mgngcngcnw snmgngcnaa yacngtnmgn wsnttycayc aygargarws nytngargar 360
ytnccngara cnwsnggnaa racnacnmgn mgnttyttyt tyaayytnws nwsnathccn 420
acngargart tyathacnws ngcngarytn cargtnttym gngarcarat gcargaygcn 480
ytnggnaaya aywsnwsntt ycaycaymgn athaayatht aygarathat haarccngcn 540
acngcnaayw snaarttycc ngtnacnmgn ytnytngaya cnmgnytngt naaycaraay 600
gcnwsnmgnt gggarwsntt ygaygtnacn ccngcngtna tgmgntggac ngcncarggn 660
caygcnaayc ayggnttygt ngtngargtn gcncayytng argaraarca rggngtnwsn 720
aarmgncayg tnmgnathws nmgnwsnytn caycargayg arcaywsntg gwsncarath 780
mgnccnytny tngtnacntt yggncaygay ggnaarggnc ayccnytnca yaarmgngar 840
aarmgncarg cnaarcayaa rcarmgnaar mgnytnaarw snwsntgyaa rmgncayccn 900
ytntaygtng ayttymgngc ngarmgnwsn athgtngcnc cnccnggnta ycaygcntty 960
taytgycayg gngartgycc nttyccnytn gcngaycayy tnaaywsnac naaycaygcn 1020
athgtncara cnytngtnaa ywsngtnaay wsnaarathc cnaargcntg ytgygtnccn 1080
acngcntayg cnggnaaryt nytnathwsn ytnwsngarg armgnathws ngcncaycay 1140
gtnccnaaya tggtngcnac ngartgyggn tgymgn 1176

<210> SEQ ID NO 55
<211> LENGTH: 1185
<212> TYPE: DNA
<213> ORGANISM: Artificial Sequence
<220> FEATURE:
<223> OTHER INFORMATION: Variant 9 preprotein gene
<220> FEATURE:
<221> NAME/KEY: misc_feature
<222> LOCATION: (0)...(0)
<223> OTHER INFORMATION: n = a, c, t, or g

<400> SEQUENCE: 55
atggtngcng gnacnmgntg yytnytngcn ytnytnytnc cncargtnyt nytnggnggn 60
gcngcnggny tngtnccnga rytnggnmgn mgnaarttyg cngcngcnws nwsnggnmgn 120
ccnwsnwsnc arccnwsnga ygargtnytn wsngarttyg arytnmgnyt nytnwsnatg 180
ttyggnytna arcarmgncc nacnccnwsn mgngaygcng tngtnccncc ntayatgytn 240
gayytntaym gnmgncayws nggncarccn ggnwsnccng cnccngayca ymgnytngar 300
mgngcngcnw snmgngcnaa yacngtnmgn wsnttycayc aygargarws nytngargar 360
ytnccngara cnwsnggnaa racnacnmgn mgnttyttyt tyaayytnws nwsnathccn 420
acngargart tyathacnws ngcngarytn cargtnttym gngarcarat gcargaygcn 480
ytnggnaaya aywsnwsntt ycaycaymgn athaayatht aygarathat haarccngcn 540
acngcnaayw snaarttycc ngtnacnmgn ytnytngaya cnmgnytngt naaycaraay 600
gcnwsnmgnt gggarwsntt ygaygtnacn ccngcngtna tgmgntggac ngcncarggn 660
caygcnaayc ayggnttygt ngtngargtn gcncayytng argaraarca rggngtnwsn 720
aarmgncayg tnmgnathws nmgnwsnytn caycargayg arcaywsntg gwsncarath 780
mgnccnytny tngtnacntt yggncaygay ggnaarggnc ayccnytnca yaarmgngar 840
aarmgncarg cnaarcayaa rcarmgnaar mgnytnaarw snwsntgyaa rmgncayccn 900
ytntaygtng ayttywsnga ygtnggntgg aaygaytgga thgtngcncc nccnggntay 960
caygcnttyt aytgycaygg ngartgyccn ttyccnytng cngaycayyt naaywsnacn 1020
aaycaygcna thgtncarac nytngtnaay wsngtnaayw snaarathcc naargcntgy 1080
tgygtnccna cngcntaygc nggnaarytn ytnathwsny tnwsngarga rmgnathwsn 1140
gcncaycayg tnccnaayat ggtngtngar ggntgyggnt gymgn 1185

<210> SEQ ID NO 56
<211> LENGTH: 1176
<212> TYPE: DNA
<213> ORGANISM: Artificial Sequence
<220> FEATURE:
<223> OTHER INFORMATION: Variant 10 preprotein gene
<220> FEATURE:
<221> NAME/KEY: misc_feature
<222> LOCATION: (0)...(0)
<223> OTHER INFORMATION: n = a, c, t, or g

<400> SEQUENCE: 56
atggtngcng gnacnmgntg yytnytngcn ytnytnytnc cncargtnyt nytnggnggn 60
gcngcnggny tngtnccnga rytnggnmgn mgnaarttyg cngcngcnws nwsnggnmgn 120
ccnwsnwsnc arccnwsnga ygargtnytn wsngarttyg arytnmgnyt nytnwsnatg 180
ttyggnytna arcarmgncc nacnccnwsn mgngaygcng tngtnccncc ntayatgytn 240
gayytntaym gnmgncayws nggncarccn ggnwsnccng cnccngayca ymgnytngar 300
mgngcngcnw snmgngcnaa yacngtnmgn wsnttycayc aygargarws nytngargar 360
ytnccngara cnwsnggnaa racnacnmgn mgnttyttyt tyaayytnws nwsnathccn 420
acngargart tyathacnws ngcngarytn cargtnttym gngarcarat gcargaygcn 480
ytnggnaaya aywsnwsntt ycaycaymgn athaayatht aygarathat haarccngcn 540
acngcnaayw snaarttycc ngtnacnmgn ytnytngaya cnmgnytngt naaycaraay 600
gcnwsnmgnt gggarwsntt ygaygtnacn ccngcngtna tgmgntggac ngcncarggn 660
caygcnaayc ayggnttygt ngtngargtn gcncayytng argaraarca rggngtnwsn 720
aarmgncayg tnmgnathws nmgnwsnytn caycargayg arcaywsntg gwsncarath 780
mgnccnytny tngtnacntt yggncaygay ggnaarggnc ayccnytnca yaarmgngar 840
aarmgncarg cnaarcayaa rcarmgnaar mgnytnaarw snwsntgyaa rmgncayccn 900
ytntaygtng ayttymgngc ngarmgnwsn athgtngcnc cnccnggnta ycaygcntty 960
taytgycayg gngartgycc nttyccnytn gcngaycayy tnaaywsnac naaycaygcn 1020
athgtncara cnytngtnaa ywsngtnaay wsnaarathc cnaargcntg ytgygtnccn 1080
acngcntayg cnggnaaryt nytnathwsn ytnwsngarg armgnathws ngcncaycay 1140
gtnccnaaya tggtngtnga rggntgyggn tgymgn 1176

<210> SEQ ID NO 57
<211> LENGTH: 1185
<212> TYPE: DNA
<213> ORGANISM: Artificial Sequence
<220> FEATURE:
<223> OTHER INFORMATION: Variant 11 preprotein gene
<220> FEATURE:
<221> NAME/KEY: misc_feature
<222> LOCATION: (0)...(0)
<223> OTHER INFORMATION: n = a, c, t, or g

<400> SEQUENCE: 57
atggtngcng gnacnmgntg yytnytngcn ytnytnytnc cncargtnyt nytnggnggn 60
gcngcnggny tngtnccnga rytnggnmgn mgnaarttyg cngcngcnws nwsnggnmgn 120
ccnwsnwsnc arccnwsnga ygargtnytn wsngarttyg arytnmgnyt nytnwsnatg 180
ttyggnytna arcarmgncc nacnccnwsn mgngaygcng tngtnccncc ntayatgytn 240
gayytntaym gnmgncayws nggncarccn ggnwsnccng cnccngayca ymgnytngar 300
mgngcngcnw snmgngcnaa yacngtnmgn wsnttycayc aygargarws nytngargar 360
ytnccngara cnwsnggnaa racnacnmgn mgnttyttyt tyaayytnws nwsnathccn 420
acngargart tyathacnws ngcngarytn cargtnttym gngarcarat gcargaygcn 480
ytnggnaaya aywsnwsntt ycaycaymgn athaayatht aygarathat haarccngcn 540
acngcnaayw snaarttycc ngtnacnmgn ytnytngaya cnmgnytngt naaycaraay 600
gcnwsnmgnt gggarwsntt ygaygtnacn ccngcngtna tgmgntggac ngcncarggn 660
caygcnaayc ayggnttygt ngtngargtn gcncayytng argaraarca rggngtnwsn 720
aarmgncayg tnmgnathws nmgnwsnytn caycargayg arcaywsntg gwsncarath 780
mgnccnytny tngtnacntt yggncaygay ggnaarggnc ayccnytnca yaarmgngar 840
aarmgncarg cnaarcayaa rcarmgnaar mgnytnaarw snwsntgyaa rmgncayccn 900
ytntaygtng ayttywsnga ygtnggntgg aaygaytgga thgtngcncc nccnggntay 960
caygcnttyt aytgycaygg ngartgyccn ttyccnytng cngaycayyt naaywsnacn 1020
aaycaygcna thgtncarac nytngtnaay wsngtnaayw snaarathcc naargcntgy 1080
tgygtnccna cngarytngc nggnaarytn ytnathwsny tnwsngarga rmgnathwsn 1140
gcncaycayg tnccnaayat ggtngtngar ggntgyggnt gymgn 1185

<210> SEQ ID NO 58
<211> LENGTH: 1176
<212> TYPE: DNA
<213> ORGANISM: Artificial Sequence
<220> FEATURE:
<223> OTHER INFORMATION: Variant 12 preprotein gene
<220> FEATURE:
<221> NAME/KEY: misc_feature
<222> LOCATION: (0)...(0)
<223> OTHER INFORMATION: n = a, c, t, or g

<400> SEQUENCE: 58
atggtngcng gnacnmgntg yytnytngcn ytnytnytnc cncargtnyt nytnggnggn 60
gcngcnggny tngtnccnga rytnggnmgn mgnaarttyg cngcngcnws nwsnggnmgn 120
ccnwsnwsnc arccnwsnga ygargtnytn wsngarttyg arytnmgnyt nytnwsnatg 180

-continued

```
ttyggnytna arcarmgncc nacnccnwsn mgngaygcng tngtnccncc ntayatgytn    240
gayytntaym gnmgncayws nggncarccn ggnwsnccng cnccngayca ymgnytngar    300
mgngcngcnw snmgngcnaa yacngtnmgn wsnttycayc aygargarws nytngargar    360
ytnccngara cnwsnggnaa racnacnmgn mgnttyttyt tyaayytnws nwsnathccn    420
acngargart tyathacnws ngcngarytn cargtnttym gngarcarat gcargaygcn    480
ytnggnaaya aywsnwsntt ycaycaymgn athaayatht aygarathat haarccngcn    540
acngcnaayw snaarttycc ngtnacnmgn ytnytngaya cnmgnytngt naaycaraay    600
gcnwsnmgnt gggarwsntt ygaygtnacn ccngcngtna tgmgntggac ngcncarggn    660
caygcnaayc ayggnttygt ngtngargtn gcncayytng argaraarca rggngtnwsn    720
aarmgncayg tnmgnathws nmgnwsnytn caycargayg arcaywsntg gwsncarath    780
mgnccnytny tngtnacntt yggncaygay ggnaarggnc ayccnytnca yaarmgngar    840
aarmgncarg cnaarcayaa rcarmgnaar mgnytnaarw snwsntgyaa rmgncayccn    900
ytntaygtng ayttymgngc ngarmgnwsn athgtngcnc cnccnggnta ycaygcntty    960
taytgycayg gngartgycc nttyccnytn gcngaycayy tnaaywsnac naaycaygcn   1020
athgtncara cnytngtnaa ywsngtnaay wsnaarathc cnaargcntg ytgygtnccn   1080
acngarytng cnggnaaryt nytnathwsn ytnwsngarg armgnathws ngcncaycay   1140
gtnccnaaya tggtngtnga rggntgyggn tgymgn                             1176
```

CHIMERA OF BONE MORPHOGENIC PROTEIN 2 AND THE MÜLLERIAN-INHIBITING SUBSTANCE TYPE II RECEPTOR BINDING REGION OF MÜLLERIAN-INHIBITING SUBSTANCE

This application is a § 371 application of PCT/US2018/017799, filed Feb. 12, 2018, which claims priority under 35 U.S.C. § 119(e) to U.S. Provisional Patent Application No. 62/457,383, filed on Feb. 10, 2017. The foregoing applications are incorporated by reference herein.

FIELD OF THE INVENTION

The invention relates generally to the field of cancer therapy. More particularly, the invention relates to recombinant constructs which include portions of the Müllerian-inhibiting substance type II receptor binding region of Müllerian-inhibiting substance protein grafted onto a bone morphogenic protein 2 framework.

BACKGROUND OF THE INVENTION

Various publications, including patents, published applications, technical articles and scholarly articles are cited throughout the specification. Each of these cited publications is incorporated by reference herein, in its entirety and for all purposes.

Ovarian cancer is diagnosed in roughly 239,000 women worldwide every year, including approximately 22,000 women in the United States. High mortality is the hallmark of the disease: the overall 5-year relative survival rate in the U.S. is 45%, and for the ⅔ of women with distant or unstaged cancer at diagnosis, it is less than 27%. Despite the acute clinical need, ovarian cancer treatment has evolved very little in the past three decades, and mortality rates are relatively unchanged. Primary treatment is surgical staging and cytoreduction, followed by systemic, platinum-based combination chemotherapy, e.g., paclitaxel/cisplatin or docetaxel/carboplatin. Unfortunately, essentially all ovarian cancers—including those that initially respond to platinum therapy—eventually become chemoresistant. The inevitable outcome is disease progression and death, underscoring the imperative for new treatments.

Biologic therapies have the potential to revolutionize ovarian cancer treatment. Among the most promising disease-associated targets is Müllerian-inhibiting substance type II receptor (MISIIR, also known as the Anti-Müllerian Hormone Receptor Type II (AMHR2)). MISIIR is expressed at moderately high levels (~50,000 copies per cell) in 70% of epithelial ovarian cancers (itself accounting for 90% of all ovarian cancers) and a wide variety of other gynecological cancers, as well as some breast and prostate cancers. MISIIR has limited expression in normal tissues and is primarily observed in the ovarian surface epithelium, testes, prostate and breast.

MISIIR plays a key role in the sexual differentiation of the human embryo, whose gonads are initially bipotential. MISIIR is co-expressed on the developing female reproductive tract along with its partner activin receptor-like kinase (ALK) Type I receptor ALK2, ALK3, and/or ALK6. The natural ligand, Müllerian-inhibiting substance (MIS, also known as anti-Müllerian hormone of AMH) is a member of the transforming growth factor beta (TGF-β) superfamily and is secreted by the developing male testes. MIS forms a ternary complex with MISIIR and ALK, activating the SMAD signaling pathway and triggering apoptosis, leading to regression of the female reproductive tract. Remarkably, ovarian cancer cell lines and primary ovarian cancer cells that overexpress MISIIR retain this sensitivity to MIS-induced signaling.

MIS is effective in the in vivo setting as MISIIR "+" human tumor xenografts in immunodeficient mice and spontaneously arising mouse ovarian tumors in TgMISIIR-TAg transgenic mice (transgenic mice with the SV-40 T Antigen under control of the MISIIR promoter) respond to systemic recombinant human MIS (rhMIS) therapy. MISIIR "+" primary human ovarian cancer cells isolated from the ascities of women with advanced ovarian cancer undergo apoptosis when exposed to MIS. This indicates that this powerful embryologic signaling pathway is still functional and relevant in advanced disease.

Unfortunately, repeated attempts by both academic and industry groups to produce native MIS in quantities sufficient for clinical study have failed and the highly conserved nature of the MISIIR/MIS/ALK signaling complex and the topography of the ALK binding surface make antibody-based strategies unlikely to succeed. Human MIS is a complicated molecule; the pre-proprotein (~35 kDa) is proteolytically cleaved to release an 18-20 kDa glycosylated C-terminal domain that forms a disulfide-linked homodimer of 35-40 kDA. It is the homodimer that represents the mature, active form of the hormone. As a result, it is a very difficult molecule to express in quantity in cell culture, leaving the promise of a MIS-based treatment as yet unfulfilled.

SUMMARY OF THE INVENTION

Chimera proteins comprise MISIIR-binding segments from MIS grafted onto a BMP2 framework. The chimera proteins may be recombinantly expressed at high levels, and have the ability to bind to and stimulate MISIIR, and ALK2, ALK3, and/or ALK6 on the surface of a cell in order to induce apoptosis in the cell.

The chimera protein may comprise a mature, active form. A mature, active form of the chimera protein may comprise an amino acid sequence comprising SEQ ID NO: 3, SEQ ID NO: 4, SEQ ID NO: 5, or SEQ ID NO: 6. A mature, active form of the chimera protein comprising SEQ ID NO: 4 may comprise the amino acid sequence of SEQ ID NO: 7 or SEQ ID NO: 8. A mature, active form of the chimera protein comprising SEQ ID NO: 5 may comprise the amino acid sequence of SEQ ID NO: 9, SEQ ID NO: 10, SEQ ID NO: 11, SEQ ID NO: 12, SEQ ID NO: 13, or SEQ ID NO: 14. A mature, active form of the chimera protein comprising SEQ ID NO: 6 may comprise the amino acid sequence of SEQ ID NO: 15, SEQ ID NO: 16, or SEQ ID NO: 17.

The chimera protein may comprise a preprotein form, which form is cleaved into the mature, active form. A preprotein form of the chimera protein may comprise an amino acid sequence comprising SEQ ID NO: 20, SEQ ID NO: 21, SEQ ID NO: 22, or SEQ ID NO: 23. A preprotein form of the chimera protein comprising SEQ ID NO: 21 may comprise the amino acid sequence of SEQ ID NO: 24 or SEQ ID NO: 25. A preprotein form of the chimera protein comprising SEQ ID NO: 22 may comprise the amino acid sequence of SEQ ID NO: 26, SEQ ID NO: 27, SEQ ID NO: 28, SEQ ID NO: 29, SEQ ID NO: 30, or SEQ ID NO: 31. A preprotein form of the chimera protein comprising SEQ ID NO: 23 may comprise the amino acid sequence of SEQ ID NO: 32, SEQ ID NO: 33, or SEQ ID NO: 34.

The chimera protein may bind to both a Type I Receptor such as ALK2, ALK3, and/or ALK6, and to the MISIIR. The chimera protein preferably binds to at least the MISIIR. Binding of the chimera protein to the MISIIR and a Type I Receptor on a cell surface induces programed cell death in the targeted cell. The cell is preferably a cancer cell expressing the MISIIR. The cancer cells include, but are not limited to ovarian cancer cells, breast cancer cells, uterine cancer cells, endometrial cancer cells, fallopian tube cancer cells, mixed Müllerian tumor cell, prostate cancer cells, and lung cancer cells. Non-limiting examples of types of uterine cancer cells include stroma sarcoma cells and leiomyosarcoma cells. Non-limiting examples of types of endometrial cancer cells include endometrial carcinoma cells and uterine carcinosarcoma cells. Non-limiting examples of types of fallopian tube cancer cells include serous adenocarcinoma cells and endometrioid adenocarcinoma cells.

The chimera protein may be used in methods for inducing apoptosis in a cell expressing the MISIIR. Tumor/cancer cells expressing the MISIIR are preferred. The methods generally comprise contacting a cell expressing the MISIIR with a chimera protein, and allowing the chimera protein to bind to the MISIIR, and a Type I receptor such as ALK2, ALK3, and/or ALK6, and activate signaling, thereby inducing apoptosis in the cell. Such cells are preferably ovarian cancer cells, breast cancer cells, uterine cancer cells, endometrial cancer cells, mixed Müllerian tumor cells, prostate cancer cells, or lung cancer cells.

The chimera protein may be used in methods for treating cancers/tumors whose cells express the MISIIR and Type I receptors. The methods generally comprise administering to a patient in need thereof a chimera protein in an amount effective to stimulate the MISIIR and a Type I receptor in MISIIR-expressing tumor cells in the patient, thereby treating MISIIR-expressing tumors in the patient. The type I receptor may comprise one or more of ALK2, ALK3, and ALK6. The patient may have one or more or ovarian cancer, uterine cancer, endometrial cancer, fallopian tube cancer, breast cancer, lung cancer, prostate cancer, or a mixed müllerian tumor. The chimera protein may be administered to the patient in a mature, active form, or may be administered to the patient in a preprotein form, with the preprotein form being cleaved into the mature, active form within the patient's body. The methods may further comprise administering a chemotherapeutic agent to the patient and/or irradiating the cancer cells in the patient. The patient is preferably a human being.

DETAILED DESCRIPTION OF THE INVENTION

Figure 1:
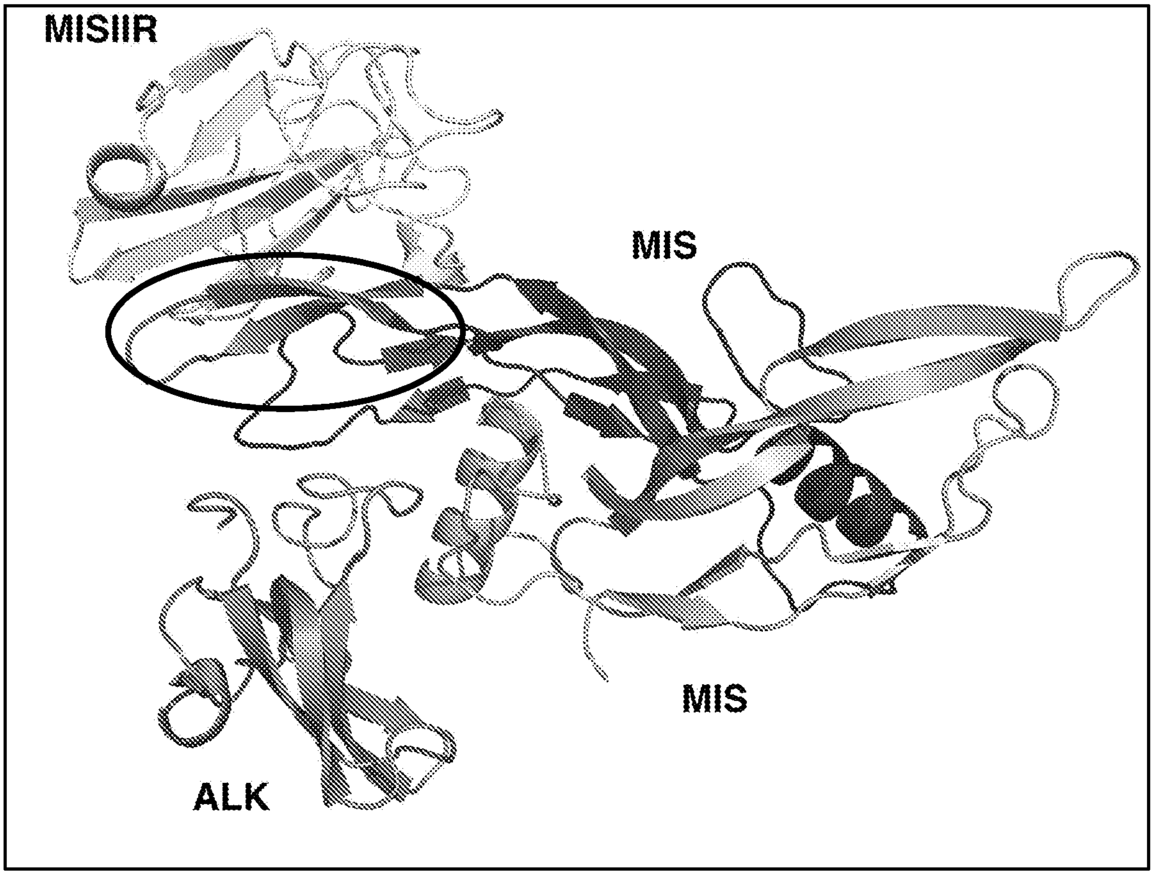
FIG. 1 shows a homology model of the MIS dimer bound to MISIIR and ALK. The MISIIR interaction loop on MIS is circled.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

The terms "subject" or "patient" are used interchangeably and refer to any animal. Mammals are preferred, and include companion and farm mammals, as well as rodents, including mice, rabbits, and rats, and other rodents. Primates are more preferred, and human beings are highly preferred.

As used herein, the singular forms "a," "an," and "the" include plural referents unless expressly stated otherwise.

It has been observed in accordance with the invention that a specialized segment of the MIS protein mediates binding between the MIS protein and the MIS type II receptor (MISIIR). To boost the expression potential of a MISIIR ligand, this segment was isolated and grafted onto a bone morphogenic protein 2 (BMP2) background, which includes regions that mediate binding to the Type I receptors ALK2, ALK3, and ALK6. The resulting chimeric protein, a hybrid between MIS and BMP2, was then further varied to optimize MISIIR binding. The MIS-BMP2 chimera and variants thereof are capable of binding to the MISIIR, as well as one or more of ALK2, ALK3, and ALK6 on epithelial cells, particularly epithelial cancer cells that express this receptor, and thereby of inducing a death signal and attendant apoptosis in such cells.

It is believed that BMP2 comprises at least two natural forms, a preprotein form (e.g., SEQ ID NO: 18), and a mature, active form (e.g., SEQ ID NO: 1). The mature, active form of BMP2 is cleaved from the preprotein form. It is believed that the cleavage site lies between the arginine at position 282 of SEQ ID NO: 18 and the glutamine at position 283 of SEQ ID NO: 18. Thus, the BMP2-MIS chimera proteins may comprise a preprotein form or a mature, active form. The preprotein portion of the chimera may comprise a polypeptide portion comprising the amino acid sequence from the methionine at position 1 of SEQ ID NO: 18 through the arginine at position 282 of SEQ ID NO: 18. The preprotein polypeptide portion may be cleaved from the chimera, thereby producing the mature, active form of the chimera. Without intending to be limited to any particular theory or mechanism of action, it is believed that the preprotein form is cleaved naturally in vivo.

In some aspects, a chimera protein comprises a mature, active form. A mature, active form of the chimera protein may comprise an amino acid sequence comprising SEQ ID NO: 3, SEQ ID NO: 4, SEQ ID NO: 5, or SEQ ID NO: 6.

In some detailed aspects, a protein comprising SEQ ID NO: 4 may comprise the amino acid sequence of SEQ ID NO: 7 or SEQ ID NO: 8. In some detailed aspects, a protein comprising SEQ ID NO: 5 may comprise the amino acid sequence of SEQ ID NO: 9, SEQ ID NO: 10, SEQ ID NO: 11, SEQ ID NO: 12, SEQ ID NO: 13, or SEQ ID NO: 14. In some detailed aspects, a protein comprising SEQ ID NO: 6 may comprise the amino acid sequence of SEQ ID NO: 15, SEQ ID NO: 16, or SEQ ID NO: 17.

In some aspects, a chimera protein comprises a preprotein form, which form is cleaved into the mature, active form. The preprotein form may have biologic activity, although the mature, active form that follows cleavage has more biologic activity than the preprotein form. A preprotein form of the chimera protein may comprise an amino acid sequence comprising SEQ ID NO: 20, SEQ ID NO: 21, SEQ ID NO: 22, or SEQ ID NO: 23.

In some detailed aspects, a protein comprising SEQ ID NO: 21 may comprise the amino acid sequence of SEQ ID NO: 24 or SEQ ID NO: 25. In some detailed aspects, a protein comprising SEQ ID NO: 22 may comprise the amino acid sequence of SEQ ID NO: 26, SEQ ID NO: 27, SEQ ID NO: 28, SEQ ID NO: 29, SEQ ID NO: 30, or SEQ ID NO: 31. In some detailed aspects, a protein comprising SEQ ID NO: 23 may comprise the amino acid sequence of SEQ ID NO: 32, SEQ ID NO: 33, or SEQ ID NO: 34.

The chimera proteins may comprise amino acid substitutions or replacements that retain the biological properties of the parent proteins. The amino acid variations are preferably conservative, but may be non-conservative. In some aspects, the chimera protein may comprise conservative amino acid variations in the amino acid sequence of SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17. In some aspects, the chimera protein may comprise conservative amino acid variations in the amino acid sequence of SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34. Chimera proteins that comprise conservative amino acid variations retain the capacity to bind to activin receptor-like kinase (ALK), preferably ALK2, ALK3, and ALK6, and to the MISIIR, and induce apoptosis in cells expressing ALK and the MISIIR on their surface, as described or exemplified herein.

In some aspects, the chimera protein may comprise variants having at least about 90%, at least about 92%, at least about 95%, at least about 96%, at least about 97%, at least about 98%, or at least about 99% sequence identity with the amino acid sequence of SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17, which variants retain the capacity to bind to one or more of ALK2, ALK3, and ALK6, and to the MISIIR, and induce apoptosis in cells expressing ALK, preferably ALK2, ALK3, and/or ALK6, and the MISIIR on their surface, as described or exemplified herein. In some aspects, the chimera protein may comprise variants having at least about 90%, at least about 92%, at least about 95%, at least about 96%, at least about 97%, at least about 98%, or at least about 99% sequence identity with the amino acid sequence of SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34, which variants retain the capacity to bind to ALK, preferably ALK2, ALK3, and/or ALK6, and to the MISIIR, and induce apoptosis in cells expressing ALK, preferably ALK2, ALK3, and/or ALK6, and the MISIIR on their surface, as described or exemplified herein.

The chimera protein preferably is capable of binding to both an activin receptor-like kinase (ALK), preferably ALK2, ALK3, and ALK6, and to the MISIIR. Thus, biologic activity of the chimera protein includes binding to an ALK and/or to the MISIIR. In preferred aspects, the ALK comprises ALK2, ALK3, or ALK6. Binding of the chimera to the ALK and to the MISIIR activates the ALK or the MISIIR and induces a death signal that, in turn, induces a cell expressing the ALK or the MISIIR to undergo apoptosis. Thus, in preferred aspects, the chimera, upon binding to the MISIIR and an ALK in a cell expressing the MISIIR, induces apoptosis in the cell.

The chimera proteins are useful, for example, as cancer therapeutics such that the chimera proteins may be targeted to cancer cells expressing the MISIIR, and preferably also expressing an ALK, more preferably also expressing one or more of ALK2, ALK3, and ALK6. Thus, in highly preferred aspects, the chimera, upon binding to the MISIIR and an ALK in a cancer cell expressing the MISIIR and the ALK, induces apoptosis in the cancer cell. The cancer cell may be any cancer cell expressing the MISIIR and the ALK. Non-limiting examples of such cancer cells include ovarian cancer cells, breast cancer cells, uterine cancer cells, endometrial cancer cells, fallopian cancer cells, mixed Müllerian tumor cells, prostate cancer cells, and lung cancer cells. Non-limiting examples of types of uterine cancer cells include stroma sarcoma cells and leiomyosarcoma cells. Non-limiting examples of types of endometrial cancer cells include endometrial carcinoma cells and uterine carcinosarcoma cells. Non-limiting examples of types of fallopian tube cancer cells include serous adenocarcinoma cells and endometrioid adenocarcinoma cells.

The chimera proteins may comprise post-translational modifications or moieties. For example, the chimera proteins may be methylated, acetylated, glycosylated, sulfated, phosphorylated, carboxylated, and amidated moieties and other moieties that are well known in the art. Moieties include any chemical group or combinations of groups commonly found on the BMP2 or MIS molecules in nature, or otherwise added to proteins by particular recombinant expression systems, including prokaryotic and eukaryotic expression systems.

The chimera proteins may optionally be labeled, fused, or conjugated to any chemical or biomolecule moieties. Labeled chimera proteins may find use in therapeutic, diagnostic, or basic research applications. Such labels/conjugates can be detectable, such as fluorochromes, radiolabels, enzymes, fluorescent proteins, and biotin. The labels/conjugates may be chemotherapeutic agents, toxins, isotopes, and other agents used for treating conditions such as the killing of cancer cells. In the case of treating tumors, the agent may be among the class of alkylating agents, antimetabolites, anthracyclines, antibiotics, platinums, plant alkaloids, vinca alkaloids, topoisomerase inhibitors, taxanes, hormones, corticosteroids, epipodophyllotoxins, toxins, and other agents known or used to treat any aspect of tumor growth, sustenance, or proliferation, including the killing of the tumor cells or inhibition of angiogenesis or neovascularization of a tumor.

The chimera proteins may optionally be labeled, fused or conjugated to a peptide, another protein or an oligonucleotide. Labeled chimera proteins may improve, alter, or broaden the targeting properties of the chimera. Such labels, fusions, or conjugates of the chimera may be used in therapeutic, diagnostic, or basic research applications. Suitable labels and conjugates include peptides, proteins or targeting agents. Non-limiting examples of such agents include targeting peptides, DARPins, affibodies, anticalins, avimers, affitins, affins, fynomers, kunitz domain peptides, monobodies, centryns, single chain antibodies, antibody fragments and intact antibodies.

Polynucleotide sequences that encode the preprotein form and mature, active form of the chimera proteins are featured, as are the respective complement of such sequences. Polynucleotides include, but are not limited to, RNA, DNA, cDNA, hybrids of RNA and DNA, and single, double, or triple stranded strands of RNA, DNA, or hybrids thereof.

In some aspects, a polynucleotide encoding a mature, active form of the chimera comprises a nucleic acid sequence encoding the amino acid sequence of SEQ ID NO: 3, SEQ ID NO: 4, SEQ ID NO: 5, or SEQ ID NO: 6. In some aspects, a polynucleotide encoding a mature, active form of the chimera comprises a nucleic acid sequence encoding the amino acid sequence of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17. In some aspects, a polynucleotide encoding a mature, active form of the chimera comprises the nucleic acid sequence of SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, or SEQ ID NO: 46.

In some aspects, a polynucleotide encoding a preprotein form of the chimera comprises a nucleic acid sequence encoding the amino acid sequence of SEQ ID NO: 20, SEQ ID NO: 21, SEQ ID NO: 22, or SEQ ID NO: 23. In some aspects, a polynucleotide encoding a mature, active form of the chimera comprises a nucleic acid sequence encoding the amino acid sequence of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34. In some aspects, a polynucleotide encoding preprotein form of the chimera comprises the nucleic acid sequence of SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, or SEQ ID NO: 58.

Also featured are vectors comprising the polynucleotides. The vectors may be expression vectors. Recombinant expression vectors containing a sequence encoding a protein of interest are thus provided. The expression vector may contain one or more additional sequences, such as but not limited to regulatory sequences, a selection marker, a purification tag, or a polyadenylation signal. Such regulatory elements may include a transcriptional promoter, enhancers, mRNA ribosomal binding sites, or sequences that control the termination of transcription and translation.

Expression vectors, especially mammalian expression vectors, may include one or more nontranscribed elements, such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a specific host may also be incorporated.

The vectors may be used to transform any of a wide array of host cells known to those of skill in the art, and preferably host cells capable of expressing the chimera proteins. Vectors include without limitation, plasmids, phagemids, cosmids, baculoviruses, bacmids, bacterial artificial chromosomes (BACs), yeast artificial chromosomes (YACs), and baculovirus, as well as other bacterial, eukaryotic, yeast, and viral vectors. Suitable host cells include without limitation CHO cells, HEK293 cells, or any eukaryotic stable cell line known or produced, and also include bacteria, yeast, and insect cells.

The disclosure also features compositions comprising one or more of the chimera proteins (in the preprotein form or mature, active form). These compositions may further comprise at least one of any suitable auxiliary, such as, but not limited to one or more, diluents, binders, stabilizers, buffers, salts, lipophilic solvents, preservatives, adjuvants, or other suitable carrier and/or excipient. Pharmaceutically acceptable auxiliaries are preferred. The compositions may comprise any of the chimera proteins described and/or exemplified herein and an acceptable carrier such as a pharmaceutically acceptable carrier. Suitable carriers include any media that does not interfere with the biological activity of the chimera and preferably is not toxic to a host to which it is administered. The carrier may be an aqueous solution, such as water, saline, or alcohol, or a physiologically compatible buffer, such as Hanks's solution, Ringer's solution, or physiological saline buffer. The carrier may contain formulatory agents, such as suspending, stabilizing and/or dispersing agents.

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administrations. The compositions may be formulated in a suitable controlled-release vehicle, with an adjuvant, or as a depot formulation.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions.

The chimera proteins may be used, for example, to induce apoptosis in cells that express the MISIIR and an ALK, preferably one or more of ALK2, ALK3, and ALK6, on their cell surface. The chimera protein binds to the surface MISIIR and activates the MISIIR, and also binds to the ALK and activates the ALK, thereby inducing apoptosis in the cell to which the chimera protein binds. Thus, methods for inducing apoptosis in a cell are provided. The cell is preferably a cancer cell. The methods may be carried out in vitro, in vivo, ex vivo, or in situ.

In some aspects, methods for inducing apoptosis in a cell comprise contacting a cell expressing the MISIIR and ALK with one or more chimera proteins in an amount effective to stimulate the MISIIR and ALK, thereby inducing apoptosis in the cell. The ALK may comprise one or more of ALK2, ALK3, and ALK6. The one or more chimera proteins may be any chimera protein(s) described or exemplified herein. The chimera protein(s) is/are preferably in a mature, active form, though the chimera protein(s) may be in the preprotein form. In some aspects, a chimera protein comprises a mature, active form comprising the amino acid sequence of SEQ ID NO: 3, SEQ ID NO: 4, SEQ ID NO: 5, or SEQ ID NO: 6. In some aspects, a chimera protein comprises a mature, active form comprising the amino acid sequence of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17. In some aspects, a chimera protein comprises a preprotein form comprising the amino acid sequence of SEQ ID NO: 20, SEQ ID NO: 21, SEQ ID NO: 22, or SEQ ID NO: 23. In some aspects, a chimera protein comprises a preprotein form comprising the amino acid sequence of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34.

The one or more chimera proteins may be used to induce apoptosis in any cell expressing the MISIIR and an ALK. Tumor/cancer cells expressing the MISIIR are preferred. Cancer cells include, but are not limited to ovarian cancer cells, breast cancer cells, uterine cancer cells, endometrial cancer cells, fallopian tube cancer cells, mixed Müllerian tumor cells, prostate cancer cells, and lung cancer cells. The one or more chimera proteins may be comprised in a composition comprising the protein(s) and a carrier. The carrier may be a pharmaceutically acceptable carrier. The composition may comprise an auxiliary.

The cells may be comprised in a tumor. For example, the chimera protein may be contacted with cells in a tumor, thereby inducing apoptosis in MISIIR-expressing cells within the tumor, thereby treating the tumor. The tumor may comprise a tumor of the ovary, a tumor of the breast, a tumor of the uterus, a tumor of the endometrium, a tumor of the fallopian tube, a tumor of the prostate gland, or a tumor of the lung. In some aspects, the methods may further comprise administering to the tumor a chemotherapeutic agent. In some aspects, the methods may further comprise irradiating the tumor.

The one or more chimera proteins or composition comprising the protein(s) may be administered directly to the tumor, including any substructure or location in the tumor. The one or more chimera proteins or composition comprising the protein(s) may be administered proximally to the tumor, including any location not directly in, but proximal to the tumor such that the chimera protein diffuses to and/or into the tumor, or can be actively targeted to the tumor. The one or more chimera proteins or composition comprising the protein(s) may be administered distally to the tumor, such that the chimera protein diffuses to and/or into the tumor. Diffusion may be passive (e.g., via blood flow). Proximally or distally administered chimera proteins or compositions comprising the protein may also be actively targeted to the tumor. In some highly preferred aspects, the composition is administered to the vascular endothelium of the tumor.

The one or more chimera proteins may be used, for example, to treat tumors by inducing apoptosis in cells within the tumor which express the MISIIR on their cell surface. Thus, methods for treating tumors expressing the MISIIR are provided. The cells preferably also express an ALK on their surface. The ALK preferably comprises one or more of ALK2, ALK3, and ALK6. Thus, methods for treating tumors expressing the MISIIR and an ALK are provided.

In some aspects, the methods comprise treating ovarian cancer. The methods comprise administering to an ovarian cancer patient in need thereof one or more chimera proteins in an amount effective to stimulate the MISIIR and an ALK in ovarian tumor cells in the patient that express the MISIIR and the ALK, thereby treating ovarian cancer in the patient. The chimera protein(s) may be administered to the patient in a mature, active form, or may be administered to the patient in a preprotein form, with the preprotein form being cleaved into the mature, active form within the patient's body. The natural cell and biochemical process within the patient's body cleave the preprotein form. The chimera protein(s) (mature, active or preprotein) may be any chimera protein described or exemplified herein. The method may further comprise administering a chemotherapeutic agent to the patient and/or irradiating the cancer cells in the patient.

In some aspects, the methods comprise treating breast cancer. The methods comprise administering to a breast cancer patient in need thereof one or more chimera proteins in an amount effective to stimulate the MISIIR and an ALK in breast tumor cells in the patient that express the MISIIR and the ALK, thereby treating breast cancer in the patient. The chimera protein(s) may be administered to the patient in a mature, active form, or may be administered to the patient in a preprotein form, with the preprotein form being cleaved into the mature, active form within the patient's body. The natural cell and biochemical process within the patient's body cleave the preprotein form. The chimera protein(s) (mature, active or preprotein) may be any chimera protein described or exemplified herein. The method may further comprise administering a chemotherapeutic agent to the patient and/or irradiating the cancer cells in the patient.

In some aspects, the methods comprise treating prostate cancer. The methods comprise administering to a prostate cancer patient in need thereof one or more chimera proteins in an amount effective to stimulate the MISIIR and an ALK in prostate tumor cells in the patient that express the MISIIR and the ALK, thereby treating prostate cancer in the patient. The chimera protein(s) may be administered to the patient in a mature, active form, or may be administered to the patient in a preprotein form, with the preprotein form being cleaved into the mature, active form within the patient's body. The natural cell and biochemical process within the patient's body cleave the preprotein form. The chimera protein(s) (mature, active or preprotein) may be any chimera protein described or exemplified herein. The method may further comprise administering a chemotherapeutic agent to the patient and/or irradiating the cancer cells in the patient.

In some aspects, the methods comprise treating lung cancer. The methods comprise administering to a lung cancer patient in need thereof one or more chimera proteins in an amount effective to stimulate the MISIIR and an ALK in lung tumor cells in the patient that express the MISIIR and the ALK, thereby treating lung cancer in the patient. The chimera protein(s) may be administered to the patient in a mature, active form, or may be administered to the patient in a preprotein form, with the preprotein form being cleaved into the mature, active form within the patient's body. The natural cell and biochemical process within the patient's body cleave the preprotein form. The chimera protein(s) (mature, active or preprotein) may be any chimera protein described or exemplified herein. The method may further comprise administering a chemotherapeutic agent to the patient and/or irradiating the cancer cells in the patient.

In some aspects, the methods comprise treating uterine cancer. The methods comprise administering to a uterine cancer patient in need thereof one or more chimera proteins in an amount effective to stimulate the MISIIR and an ALK in uterine tumor cells in the patient that express the MISIIR and the ALK, thereby treating uterine cancer in the patient. The uterine cancer may comprise stroma sarcoma or leiomyosarcoma. The chimera protein(s) may be administered to the patient in a mature, active form, or may be administered to the patient in a preprotein form, with the preprotein form being cleaved into the mature, active form within the patient's body. The natural cell and biochemical process within the patient's body cleave the preprotein form. The chimera protein(s) (mature, active or preprotein) may be any chimera protein described or exemplified herein. The method may further comprise administering a chemotherapeutic agent to the patient and/or irradiating the cancer cells in the patient.

In some aspects, the methods comprise treating endometrial cancer. The methods comprise administering to an endometrial cancer patient in need thereof one or more chimera proteins in an amount effective to stimulate the MISIIR and an ALK in endometrium tumor cells in the patient that express the MISIIR and the ALK, thereby treating endometrial cancer in the patient. The endometrial cancer may comprise endometrial carcinoma or uterine carcinosarcoma. The chimera protein(s) may be administered to the patient in a mature, active form, or may be administered to the patient in a preprotein form, with the preprotein form being cleaved into the mature, active form within the patient's body. The natural cell and biochemical process within the patient's body cleave the preprotein form.

The chimera protein(s) (mature, active or preprotein) may be any chimera protein described or exemplified herein. The method may further comprise administering a chemotherapeutic agent to the patient and/or irradiating the cancer cells in the patient.

In some aspects, the methods comprise treating fallopian tube cancer. The methods comprise administering to a fallopian tube cancer patient in need thereof one or more chimera proteins in an amount effective to stimulate the MISIIR and an ALK in fallopian tube tumor cells in the patient that express the MISIIR and the ALK, thereby treating fallopian tube cancer in the patient. The fallopian tube cancer may comprise serous adenocarcinoma or endometrioid adenocarcinoma. The chimera protein(s) may be administered to the patient in a mature, active form, or may be administered to the patient in a preprotein form, with the preprotein form being cleaved into the mature, active form within the patient's body. The natural cell and biochemical process within the patient's body cleave the preprotein form. The chimera protein(s) (mature, active or preprotein) may be any chimera protein described or exemplified herein. The method may further comprise administering a chemotherapeutic agent to the patient and/or irradiating the cancer cells in the patient.

In some aspects, the methods comprise treating a mixed Müllerian tumor. The methods comprise administering to a mixed Müllerian tumor patient in need thereof one or more chimera proteins in an amount effective to stimulate the MISIIR and an ALK in mixed Müllerian tumor cells in the patient that express the MISIIR and the ALK, thereby treating a mixed Müllerian tumor in the patient. The chimera protein(s) may be administered to the patient in a mature, active form, or may be administered to the patient in a preprotein form, with the preprotein form being cleaved into the mature, active form within the patient's body. The natural cell and biochemical process within the patient's body cleave the preprotein form. The chimera protein(s) (mature, active or preprotein) may be any chimera protein described or exemplified herein. The method may further comprise administering a chemotherapeutic agent to the patient and/or irradiating the cancer cells in the patient.

Use of a chimera protein in the treatment of cancers/tumors are provided. The cancers/tumors preferably express the MISIIR, more preferably also express an ALK, and more preferably also express one or more of ALK2, ALK3, and ALK6. The chimera protein may comprises a mature, active form comprising the amino acid sequence of SEQ ID NO: 3, SEQ ID NO: 4, SEQ ID NO: 5, or SEQ ID NO: 6. The mature, active form may comprise the amino acid sequence of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17. The chimera protein may comprise a preprotein form comprising the amino acid sequence of SEQ ID NO: 20, SEQ ID NO: 21, SEQ ID NO: 22, or SEQ ID NO: 23. The preprotein form may comprise the amino acid sequence of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34. Any of these chimera proteins or proteins otherwise described and exemplified herein may be for use as a medicament. Any of these chimera proteins or proteins otherwise described and exemplified herein may be for use in the manufacture of a medicament. Any of these chimera proteins or proteins otherwise described and exemplified herein may be for use in treating ovarian cancer. Any of these chimera proteins or proteins otherwise described and exemplified herein may be for use in treating breast cancer. Any of these chimera proteins or proteins otherwise described and exemplified herein may be for use in treating prostate cancer. Any of these chimera proteins or proteins otherwise described and exemplified herein may be for use in treating lung cancer. Any of these chimera proteins or proteins otherwise described and exemplified herein may be for use in treating uterine cancer. Any of these chimera proteins or proteins otherwise described and exemplified herein may be for use in treating endometrial cancer. Any of these chimera proteins or proteins otherwise described and exemplified herein may be for use in treating a mixed Müllerian tumor.

Kits for use in practicing the methods described and exemplified herein are provided. The kits may be used to supply the chimera proteins (either or both of the mature, active forms and preprotein forms) and other agents for use in diagnostic, basic research, or therapeutic methods, among others.

In some aspects, a kit comprises a chimera protein comprising the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34, or any combination thereof, and instructions for using the chimera protein or combination of chimera proteins in a method for inducing apoptosis in a cell expressing the MISIIR and an ALK, or in a method for inducing apoptosis in a tumor comprising cells expressing the MISIIR and an ALK, or in a method for treating a tumor. The method for treating a tumor may comprise a method for treating ovarian cancer, a method for treating breast cancer, a method for treating prostate cancer, a method for treating lung cancer, a method for treating uterine cancer, a method for treating endometrial cancer, a method for treating fallopian tube cancer, or a method for treating a mixed Müllerian tumor. The instructions may be for using the chimera protein in any method described or exemplified herein. The chimera protein may be comprised in a composition comprising a carrier and one or more auxiliaries. The kit may comprise a device for injecting the chimera protein into a patient, including but not limited to a syringe and needle, or catheter.

The following examples are provided to describe the invention in greater detail. They are intended to illustrate, not to limit, the invention.

EXAMPLE 1

BMP2-MIS Chimera Molecule

The chimera molecule is based upon the hormone bone morphogenetic protein 2 (BMP2). Like MIS, BMP2 belongs to the TGF-β superfamily, and it binds to the same Type I receptors—activin receptor-like kinase (ALK) as MIS, although it binds to a different Type II receptor (activin type II receptor, ACVR2). BMP2 is a material capable of being used for bone mending. The natural affinity of BMP2 for ALK has been used to design several synthetic hormones, each resembling BMP2 but with the Type II binding region replaced by that of MIS. Without intending to be limited to any particular theory or mechanism of action, it is believed that the resulting chimera molecules will activate signaling through MISIIR/ALK, leading to apoptosis of the target cell.

EXAMPLE 2

Identification of Key MIS Loop

The three-dimensional structures of MIS and MISIIR have not been solved by X-ray crystallography. Accordingly, a homology model was created using closely related known structures. A crystal structure of the ternary complex of BMP2 bound to ACVR2 and BMP1R, was employed. Based on this modeling, it was determined that the binding between MIS and MISIIR is mediated by an 18-residue loop on MIS (FIG. 1). With this insight, experiments were conducted to impart specificity for MISIIR to an irrelevant scaffold to demonstrate the importance of this loop.

Figure 2:
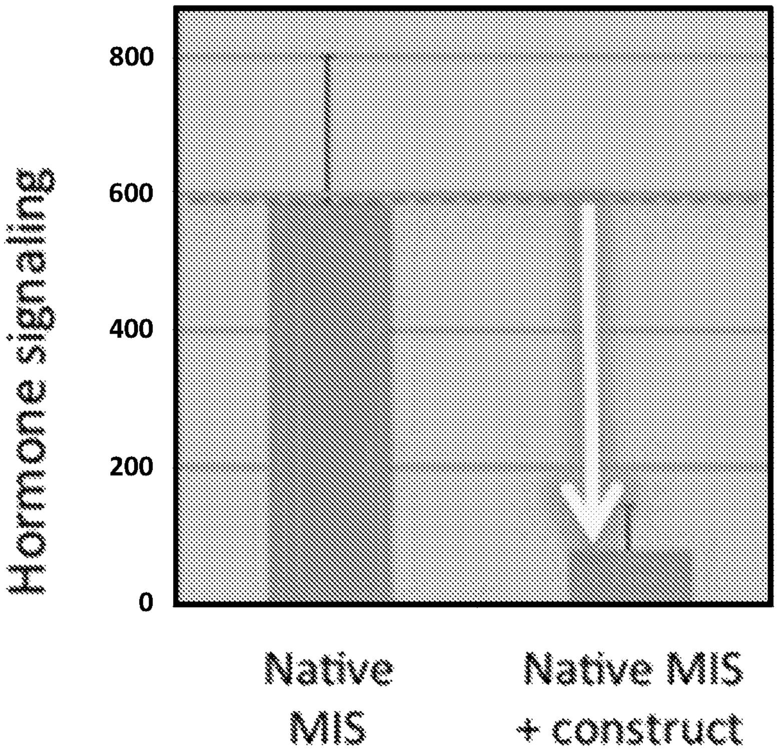
FIG. 2 shows the results of a reporter gene assay demonstrating that a MIS loop engineered into an irrelevant antibody (construct) confers the ability to block MIS binding to MISIIR and subsequent signaling.

A non-specific antibody with a compatible variable domain framework was selected, and the loop was grafted in place of the heavy chain complementarity determining region (CDR) 3 (WO/2012/166712). The ability of this MIS-loop grafted antibody to compete with native MIS for MISIIR was then tested in a competitive binding assay. The modified antibody was allowed to compete with MIS for binding to P19 neuroblastoma cells stably transfected with human MISIIR and a luciferase reporter pTLX2-Luc under control of the downstream SMAD pathway. In this assay, MIS-induced luciferase activity was observed, indicating that MIS was binding to MISIIR and ALK and inducing downstream signaling. The addition of MIS-loop containing antibody blocked signaling and luciferase activity, indicating it was engaging the MIS binding site on MISIIR but not the second site on ALK (FIG. 2) while the parental, irrelevant antibody had no effect (data not shown). This observation supports the model-based prediction that this was the key MIS binding loop for MISIIR engagement.

EXAMPLE 3

Redesign of BMP2

A goal is to develop a molecule that mimics the ability of MIS to signal for apoptosis by binding to MISIIR and ALK. Since BMP2 naturally binds to ALK, it was hypothesized that a similar approach to that described above to create the loop-grafted antibody could be used to change the type II receptor specificity of BMP2 from ACVR2 to MISIIR without affecting the ALK binding region.

Computational methods were used to determine the optimal location for the MIS loop graft within the BMP2 framework along with additional framework changes that were necessary to accommodate and properly orient the key MIS loop. Using modeling software, multiple designs were created in silico, corresponding to chimeric models comprising different regions of MIS and BMP2. Designs were selected using a scoring algorithm that prioritized designs based upon total energy. Total energy of chimera homodimers and the complex of the chimera homodimer with a model of MISIIR and ALK2 target receptors were compared and shown to be generally lower than the native dimer in complex with the model of target receptors. Twelve optimized designs have been selected for expression and testing in the experiments described in the following Examples.

EXAMPLE 4

Expression and Biophysical Characterization of the BMP2-MISIIR Binding Region Chimeras Gene synthesis. A full-length cDNA encoding human BMP2 (hBMP2) and its native secretion signal sequence, with a codon bias optimized for expression in CHO cells, will be synthesized based upon the U20S-39 clone (U.S. Pat. No. 5,618,924, ATCC cat #40345). Similarly, DNA fragments encoding variants of the hBMP2-MIS region chimera will be synthesized in the context of the U20S-39 full-length cDNA.

Protein expression. When the full-length U20S-39 encoded cDNA for hBMP2 is sub-cloned into the pMT2 vector (ATCC cat #67122) and transfected into CHO cells, the proteolytically-activated ~40 kDa hBMP2 dimer may be readily purified from conditioned cell growth media. Briefly, transient gene expression in a suspension grown CHO cells can routinely provide 1-10 mg/L quantities of recombinant protein within a short timeframe. Small-scale (30 mL) transfections and protein expressions will be carried out under serum-free conditions with the FreeStyle™ MAX system (Life Technologies) and manufacturer's recommended protocols to generate hBMP2-MIS region proteins for initial testing. CHO S cells will be transfected with vectors corresponding to all chimera designs and hBMP2, and the empty pMT2 vector will be used as a negative control. Expression and secretion of proteolytically-activated proteins into the culture media will be monitored over a 7 day time course by Western blot with a polyclonal anti-BMP2 Ab (Novus Biologicals) and purified recombinant hBMP2 will serve as a positive control (R&D Systems). It is anticipated that constructs will express to 1 mg/L but concentrations of 0.25 mg/L in culture media will be sufficient for carrying out initial biological assays. Media from each expression will be passed through 0.2 μm filter and used as source of proteins for biological assays outlined below. Scale-up expressions of lead candidates will be carried out as above with transfection and culture volumes set based upon initial expression level with a goal of obtaining 2 mg of purified protein and assuming a 50% loss during purification.

Protein purification. BMP2-MIS region chimeras and hBMP2 will be purified to >95% homogeneity using a validated two-step purification protocol that efficiently purifies hBMP2 and other TGFβ superfamily members based upon their propensity to bind both heparin sulfate affinity columns and hydrophobic interaction chromatography columns. Briefly, the conditioned serum-free media from scale-up expressions will be passed through a 0.2 μm filter, concentrated and buffer-exchanged by tangential flow dialysis and then subjected to sequential chromatography over CELLUFINE™ Sulfate (JNC Corporation) and CELLUFINE™ Butyl (JNC Corporation) columns. Behavior of expressed proteins over the columns will be monitored by Western blotting, and specific activity of the proteins at each step of purification will be measured as a function of inducing signaling in the P19 luciferase reporter cell assay described below. Purity will be assessed by SDS-PAGE.

Biophysical characterization of purified leads. Dramatic defects in physical stability associated with the chimera designs may present as an inability to express soluble protein in the culture media. However, identification of more subtle defects that will help stratify lead compounds will require a more detailed analysis. To accomplish this, dynamic light scattering (DLS) in a 96-well plate format will be employed to determine both the aggregation onset temperature (Tagg) and rates of aggregation for purified proteins. Similarly, differential scanning fluorimetry (DSF) will be used to measure the unfolding transition temperature (Tm) designs.

Contingencies. If the synthesis of one or more primary DNA sequence proves problematic, use codon redundancy will be used to circumvent this issue. An inability to express certain chimera designs will trigger a round of design optimization, incorporating data generated from clones that did express, to improve overall expression levels. Human BMP2 can also be expressed as the mature protein (amino acids 299-396 of U2OS-39, U.S. Pat. No. 5,618,924). If chimeras fail to express in sufficient quantities when produced in the context of the full-length cDNA and native signal sequences, the mature form will be expressed utilizing a heterologous leader sequences (e.g., IgK) in an effort to boost expression. Alternative purification resins (e.g., ion exchange, gel filtration) may be investigated to facilitate reaching 95% purity benchmark.

EXAMPLE 5

Biological Characterization of the BMP2-MISIIR Binding Region Chimeras

Figure 3:
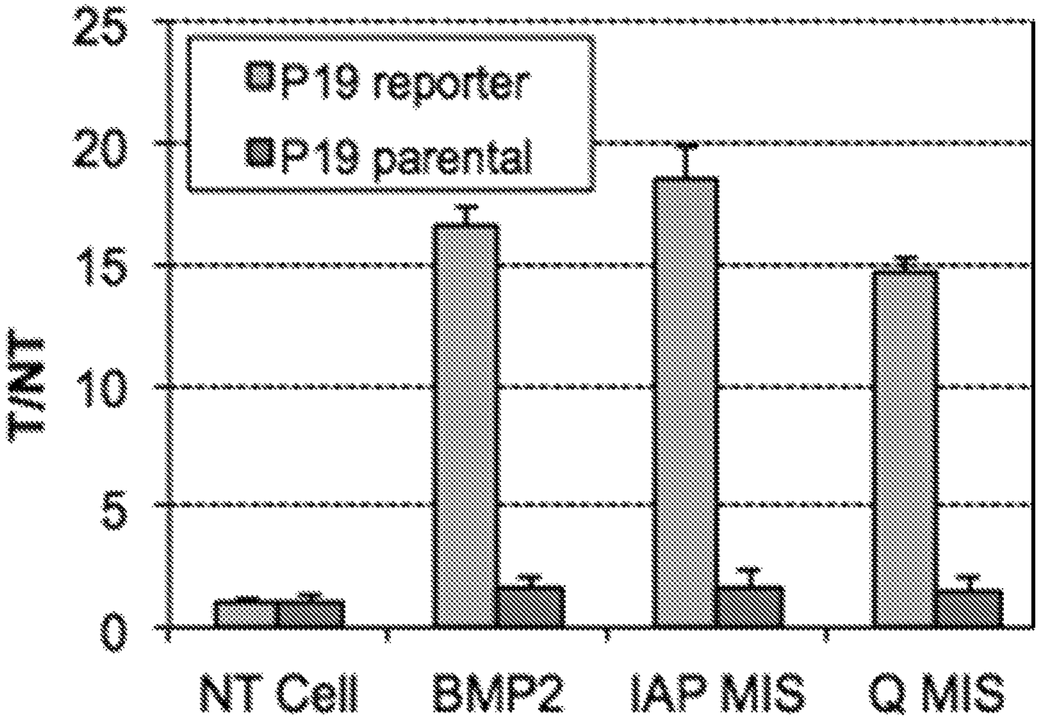
FIG. 3 shows P19 reporter cells (stably transfected with human MISIIR and the downstream luciferase reporter pTLX2-Luc) signal in the presence of BMP2 and two forms of MIS. Parental cells lacking MISIIR do not signal. T=treatment, NT=no treatment.

Screening for ability to activate signaling. As an initial functional screen, expressed proteins will be assayed for ability to induce signaling in the P19 reporter cell line, that is responsive to both MIS and BMP2. Treatment of the reporter cell line with either recombinant MIS or BMP2 at 10 nM concentrations induces expression of a luciferase reporter gene approximately 10-fold over background levels in a 3-day assay (FIG. 3). This level of induction should provide sufficient dynamic range to discriminate between fully and partially active lead agents. Briefly, P19 reporter cells, grown to sub-confluence in 96-well plates, will be treated with conditioned media from transfectants under conditions where lead agents are at 10 nM minimum concentration. Vector alone conditioned media and media spiked with 10 nM commercially available hBMP2 (R&D Systems) will serve as negative and positive controls, respectively. All experiments will be performed in triplicate and the data will be analyzed by one-way analysis of variance to determine statistical significance.

Determine specificity for MISIIR vs. Activin receptor signaling. Because chimera designs are built upon a BMP2 framework, selectivity for MISIIR vs BMP2-dependent signaling will be verified. Designs capable of eliciting signaling that is equivalent to >0.3x that seen with hBMP2 conditioned media and at least 2-fold over background will be further characterized for ability to elicit MISIIR-selective signaling.

Inhibition of OvCa cell growth. Expressed proteins preferably should maintain MIS's ability to inhibit the growth of MISIIR-positive ovarian cancer cell lines. To examine this, the MISIIR+ ovarian cancer cell line OVCAR8 will be used. MISIIR expression will be routinely verified by FACS prior to initiating experiments. Cells will be plated in a 96-well plate format and treated with conditioned media derived from each transfectant. Concentrations of 0.1-10 mg/L recombinant hMIS are believed to be sufficient to inhibit cell growth in vitro and cause regression of rat gonads in explant assays. The impact of chimeras on growth will be assessed in standard cell growth assays with CellTiter® Blue as a readout.

Differentiation of C3H10T1/2. The murine mesenchymal stem cell line C3H10T1/2 (ATCC, CCL-226), when grown in micromass cultures and treated with hBMP2 (0.1 mg/L, ~4 nM), differentiates down a chondrocyte lineage that is characterized by glycosaminoglycan production and collagen type II alpha 1 (Col2a1) expression. Induction of these markers, in the context of routine high-density micromass culture, will be used to determine the selectivity of chimera proteins for MISIIR-dependent signaling. Briefly, C3H10T1/2 cells will be harvested and resuspended at $10^7$ cells/mL in Hams's F12 media containing 10% FBS. Cells (10 μL, 105 total cells) will be plated at the center of well in 24-well plate and allowed to adhere for 2 hours. Cells will then be cultured in 1 mL of media containing 1 nM chimera protein, hBMP2, or negative control media over a two-week time course with samples taken at 7 and 14 days.

Glycosaminoglycan analysis will be carried out with Alcian Blue staining. Micromass cell pellets will be fixed with paraformaldehyde and stained with 0.5% Alcian blue in 0.1 M HCI (pH 1.0) for 12 hours. The cultures will be extracted with 6 M guanidine hydrochloride and optical density of the extracted dye measured at 630 nm. Induction of Col2a1 in similarly treated cell cultures will be monitored by Western blot analysis with commercially available antibody (Santa Cruz) and actin used as a loading control.

Identification of lead chimera. It is believed that various chimera proteins will: 1) elicit signaling in the P19 reporter assay, 2) inhibit growth of MISIIR-positive OvCa cell lines, and 3) fail to differentiate C3H10T1/2 cells down a chondrocyte lineage. Designs meeting this criteria will be purified to near homogeneity, and the $EC_{50}$ for each agent will be determined by establishing dose response curves for each purified protein in the assays outlined above.

Contingencies. If neither hBMP2 nor chimera conditioned media elicits predicted signals that meet benchmark criteria, proteins will be concentrated using single-step purification over CELLUFINE® Sulfate. Assays will then be carried out in dose-response curves using partially purified proteins to establish working concentrations for each of the constructs. The high grade serous ovarian cancer cell lines CAOV3 (ATCC: HTB-75) and CAOV4 (ATCC: HTB-76) and PDX-derived cell lines will serve as back-ups to OVCAR8. Semi-quantitative RT-PCR of Col2A1 with a validated set of primers will serve as an alternative approach to monitor C3H10T1/2 differentiation.

The invention is not limited to the embodiments described and exemplified above, but is capable of variation and modification within the scope of the appended claims.

Sequence Listing

SEQUENCE ID 1: BMP-2 mature
QAKHKQRKRLKSSCKRHPLYVDFSDVGWNDWIVAPPGYHAFYCHGECPFPLADHLNSTNHAIVQTLVNSVNS
KIPKACCVPTELSAISMLYLDENEKVVLKNYQDMVVEGCGCR -continued Sequence Listing SEQUENCE ID 2: MIS mature
AQRSAGATAADGPCALRELSVDLRAERSVLIPETYQANNCQGVCGWPQSDRNPRYGNHVVLLLKMQVRGAAL
ARPPCCVPTAYAGKLLISLSEERISAHHVPNMVATECGCR SEQUENCE ID3: Variant 2 mature
QAKHKQRKRLKSSCKRHPLYVDFSDVGWNDWIVAPPGYHAFYCHGECGWPQSDRNPRYGNHVVLLLKMQVRG
AALARPPCCVPTAYAGKLLISLSEERISAHHVPNMVATECGCR SEQUENCE ID 4: Consensus of Variant 1 and 3 mature
QAKHKQRKRLKSSCKRHPLYVDXRAERSXXXPXXYXAXXCXGXCGWPQSDRNPRYGNHVVLLLKMQVRGAAL
ARPPCCVPTAYAGKLLISLSEERISAHHVPNMVATECGCR
X23 is L or F
X29 is V or I
X30 is L or V
X31 is I or A
X33 is E or P
X34 is T or G
X36 is Q or H
X38 is N or F
X39 is N or Y
X41 is Q or H
X43 is V or E SEQUENCE ID 5: Consensus of Variants 4, 5, 6, 8, 10, and 12 mature
QAKHKQRKRLKSSCKRHPLYVDFSDVGWNDWIVAPPGYHAFYCHGECPFPLADHLNSTNHAIVQTLVNSVNS
KIPKACCVPTXXAGKLLISLSEERISAHHVPNMVXXXCGCR
X83 is A or E
X84 is Y or L
X107 is A or V
X108 is T or E
X109 is E or G SEQUENCE ID 6: Consensus of Variants 7, 9, and 11 mature
QAKHKQRKRLKSSCKRHPLYVDXRAERSXXXPXXYXAXXCXGXCPFPLADHLNSTNHAIVQTLVNSVNSK
IPKACCVPTXXAGKLLISLSEERISAHHVPNMVXXXCGCR
X23 is L or F
X29 is V or I
X30 is L or V
X31 is I or A
X33 is E or P
X34 is T or G
X36 is Q or H
X38 is N or F
X39 is N or Y
X41 is Q or H
X43 is V or E
X80 is E or A
X81 is L or Y
X104 is V or A
X105 is E or T
X106 is G or E SEQUENCE ID7: Variant 1 mature
QAKHKQRKRLKSSCKRHPLYVDLRAERSVLIPETYQANNCQGVCGWPQSDRNPRYGNHVVLLLKMQVRGAAL
ARPPCCVPTAYAGKLLISLSEERISAHHVPNMVATECGCR SEQUENCE ID8: Variant 3 mature
QAKHKQRKRLKSSCKRHPLYVDFRAERSIVAPPGYHAFYCHGECGWPQSDRNPRYGNHVVLLLKMQVRGAAL
ARPPCCVPTAYAGKLLISLSEERISAHHVPNMVATECGCR SEQUENCE ID9: Variant 4 mature
QAKHKQRKRLKSSCKRHPLYVDLRAERSVLIPETYQANNCQGVCPFPLADHLNSTNHAIVQTLVNSVNSKIP
KACCVPTAYAGKLLISLSEERISAHHVPNMVATECGCR SEQUENCE ID10: Variant 5 mature
QAKHKQRKRLKSSCKRHPLYVDLRAERSVLIPETYQANNCQGVCPFPLADHLNSTNHAIVQTLVNSVNSKIP
KACCVPTAYAGKLLISLSEERISAHHVPNMVVEGCGCR SEQUENCE ID11: Variant 6 mature
QAKHKQRKRLKSSCKRHPLYVDLRAERSVLIPETYQANNCQGVCPFPLADHLNSTNHAIVQTLVNSVNSKIP
KACCVPTELAGKLLISLSEERISAHHVPNMVVEGCGCR SEQUENCE ID12: Variant 8 mature
QAKHKQRKRLKSSCKRHPLYVDFRAERSIVAPPGYHAFYCHGECPFPLADHLNSTNHAIVQTLVNSVNSKIP
KACCVPTAYAGKLLISLSEERISAHHVPNMVATECGCR -continued

| Sequence Listing |
| --- |

SEQUENCE ID13: Variant 10 mature
QAKHKQRKRLKSSCKRHPLYVDFRAERSIVAPPGYHAFYCHGECPFPLADHLNSTNHAIVQTLVNSVNSKIP
KACCVPTAYAGKLLISLSEERISAHHVPNMVVEGCGCR SEQUENCE ID14: Variant 12 mature
QAKHKQRKRLKSSCKRHPLYVDFRAERSIVAPPGYHAFYCHGECPFPLADHLNSTNHAIVQTLVNSVNSKIP
KACCVPTELAGKLLISLSEERISAHHVPNMVVEGCGCR SEQUENCE ID15: Variant 7 mature
QAKHKQRKRLKSSCKRHPLYVDFSDVGWNDWIVAPPGYHAFYCHGECPFPLADHLNSTNHAIVQTLVNSVNS
KIPKACCVPTAYAGKLLISLSEERISAHHVPNMVATECGCR SEQUENCE ID16: Variant 9 mature
QAKHKQRKRLKSSCKRHPLYVDFSDVGWNDWIVAPPGYHAFYCHGECPFPLADHLNSTNHAIVQTLVNSVNS
KIPKACCVPTAYAGKLLISLSEERISAHHVPNMVVEGCGCR SEQUENCE ID17: Variant 11 mature
QAKHKQRKRLKSSCKRHPLYVDFSDVGWNDWIVAPPGYHAFYCHGECPFPLADHLNSTNHAIVQTLVNSVNS
KIPKACCVPTELAGKLLISLSEERISAHHVPNMVVEGCGCR SEQUENCE ID 18: BMP-2 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHP
LYVDFSDVGWNDWIVAPPGYHAFYCHGECPFPLADHLNSTNHAIVQTLVNSVNSKIPKAC
CVPTELSAISMLYLDENEKVVLKNYQDMVVEGCGCR SEQUENCE ID 19: MIS preprotein
MRDLPLTSLALVLSALGALLGTEALRAEEPAVGTSGLIFREDLDWPPGSPQEPLCLVALGGDSNGSSSPLRV
VGALSAYEQAFLGAVQRARWGPRDLATFGVCNTGDRQAALPSLRRLGAWLRDPGGQRLVVLHLEEVTWEPTP
SLRFQEPPPGGAGPPELALLVLYPGPGPEVTVTRAGLPGAQSLCPSRDTRYLVLAVDRPAGAWRGSGLALTL
QPRGEDSRLSTARLQALLFGDDHRCFTRMTPALLLLPRSEPAPLPAHGQLDTVPFPPPRPSAELEESPPSAD
PFLETLTRLVRALRVPPARASAPRLALDPDALAGFPQGLVNLSDPAALERLLDGEEPLLLLLRPTAATTGDP
APLHDPTSAPWATALARRVAAELQAAAAELRSLPGLPPATAPLLARLLALCPGGPGGLGDPLRALLLLKALQ
GLRVEWRGRDPRGPGRAQRSAGATAADGPCALRELSVDLRAERSVLIPETYQANNCQGVCGWPQSDRNPRYG
NHVVLLLKMQVRGAALARPPCCVPTAYAGKLLISLSEERISAHHVPNMVATECGCR SEQUENCE ID20: Variant 2 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDFSDVGWND
WIVAPPGYHAFYCHGECGWPQSDRNPRYGNHVVLLLKMQVRGAALARPPCCVPTAYAGKLLISLSEERISAH
HVPNMVATECGCR SEQUENCE ID 21: Consensus of Variant 1 and 3 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDXRAERSXX
XPXXYXAXXCXGXCGWPQSDRNPRYGNHVVLLLKMQVRGAALARPPCCVPTAYAGKLLISLSEERISAHHVE,
NMVATECGCR
X305 is L or F
X311 is V or I
X312 is L or V
X313 is I or A
X315 is E or P
X316 is T or G
X318 is Q or H
X320 is N or F
X321 is N or Y
X323 is Q or H
X325 is V or E SEQUENCE ID 22: Consensus of Variants 4, 5, 6, 8, 10, and 12 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA -continued

| Sequence Listing |
| --- |

TANSKFPVTRLLDTRLVNQNASRWESFDVTPAVMRWTAQGHANHGFVVEVAHLEEKQGVSKRHVRISRSLHQ
DEHSWSQIRPLLVTFGHDGKGHPLHKREKRQAKHKQRKRLKSSCKRHPLYVDFSDVGWNDWIVAPPGYHAFY
CHGECPFPLADHLNSTNHAIVQTLVNSVNSKIPKACCVPTXXAGKLLISLSEERISAHHVPNMVXXXCGCR
X365 is A or E
X366 is Y or L
X389 is A or V
X390 is T or E
X391 is E or G

SEQUENCE ID 23: Consensus of Variants 7, 9, and 11 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVSKRHVRISRSLHQ
DEHSWSQIRPLLVTFGHDGKGHPLHKREKRQAKHKQRKRLKSSCKRHPLYVDXRAERSXXXPXXYXAXXCXG
XCPFPLADHLNSTNHAIVQTLVNSVNSKIPKACCVPTXXAGKLLISLSEERISAHHVPNMVXXXCGCR
X305 is L or F
X311 is V or I
X312 is L or V
X313 is I or A
X315 is E or P
X316 is T or G
X318 is Q or H
X320 is N or F
X321 is N or Y
X323 is Q or H
X325 is V or E
X362 is E or A
X363 is L or Y
X386 is V or A
X387 is E or T
X388 is G or E SEQUENCE ID24: Variant 1 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDLRAERSVL
IPETYQANNCQGVCGWPQSDRNPRYGNHVVLLLKMQVRGAALARPPCCVPTAYAGKLLISLSEERISAHHVP
NMVATECGCR SEQUENCE ID25: Variant 3 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDFRAERSIV
APPGYHAFYCHGECGWPQSDRNPRYGNHVVLLLKMQVRGAALARPPCCVPTAYAGKLLISLSEERISAHHVP
NMVATECGCR SEQUENCE ID26: Variant 4 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDLRAERSVL
IPETYQANNCQGVCPFPLADHLNSTNHAIVQTLVNSVNSKIPKACCVPTAYAGKLLISLSEERISAHHVPNM
VATECGCR SEQUENCE ID27: Variant 5 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDLRAERSVL
IPETYQANNCQGVCPFPLADHLNSTNHAIVQTLVNSVNSKIPKACCVPTAYAGKLLISLSEERISAHHVPNM
VVEGCGCR SEQUENCE ID28: Variant 6 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDLRAERSVL
IPETYQANNCQGVCPFPLADHLNSTNHAIVQTLVNSVNSKIPKACCVPTELAGKLLISLSEERISAHHVPNM
VVEGCGCR -continued Sequence Listing SEQUENCE ID29: Variant 8 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDFRAERSIV
APPGYHAFYCHGECPFPLADHLNSTNHAIVQTLVNSVNSKIPKACCVPTAYAGKLLISLSEERISAHHVPNM
VATECGCR SEQUENCE ID30: Variant 10 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDFRAERSIV
APPGYHAFYCHGECPFPLADHLNSTNHAIVQTLVNSVNSKIPKACCVPTAYAGKLLISLSEERISAHHVPNM
VVEGCGCR SEQUENCE ID31: Variant 12 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDFRAERSIV
APPGYHAFYCHGECPFPLADHLNSTNHAIVQTLVNSVNSKIPKACCVPTELAGKLLISLSEERISAHHVPNM
VVEGCGCR SEQUENCE ID32: Variant 7 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDFSDVGWND
WIVAPPGYHAFYCHGECPFPLADHLNSTNHAIVQTLVNSVNSKIPKACCVPTAYAGKLLISLSEERISAHHV
PNMVATECGCR SEQUENCE ID33: Variant 9 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDFSDVGWND
WIVAPPGYHAFYCHGECPFPLADHLNSTNHAIVQTLVNSVNSKIPKACCVPTAYAGKLLISLSEERISAHHV
PNMVVEGCGCR SEQUENCE ID34: Variant 11 preprotein
MVAGTRCLLALLLPQVLLGGAAGLVPELGRRKFAAASSGRPSSQPSDEVLSEFELRLLSM
FGLKQRPTPSRDAVVPPYMLDLYRRHSGQPGSPAPDHRLERAASRANTVRSFHHEESLEE
LPETSGKTTRRFFFNLSSIPTEEFITSAELQVFREQMQDALGNNSSFHHRINIYEIIKPA
TANSKFPVTRLLDTRLVNQNASRWESFDVTPAVMRWTAQGHANHGFVVEVAHLEEKQGVS
KRHVRISRSLHQDEHSWSQIRPLLVTFGHDGKGHPLHKREKRQAKHKQRKRLKSSCKRHPLYVDFSDVGWND
WIVAPPGYHAFYCHGECPFPLADHLNSTNHAIVQTLVNSVNSKIPKACCVPTELAGKLLISLSEERISAHHV
PNMVVEGCGCR SEQUENCE ID35: Variant 1 mature gene
CARGCNAARCAYAARCARMGNAARMGNYTNAARWSNWSNTGYAARMGNCAYCCNYTNTAYGTNGAYYTNMGN
GCNGARMGNWSNGTNYTNATHCCNGARACNTAYCARGCNAAYAAYTGYCARGGNGTNTGYGGNTGGCCNCAR
WSNGAYMGNAAYCCNMGNTAYGGNAAYCAYGTNGTNYTNYTNYTNAARATGCARGTNMGNGGNGCNGCNYTN
GCNMGNCCNCCNTGYTGYGTNCCNACNGCNTAYGCNGGNAARYTNYTNATHWSNYTNWSNGARGARMGNATH
WSNGCNCAYCAYGTNCCNAAYATGGTNGCNACNGARTGYGGNTGYMGN SEQUENCE ID36: Variant 2 mature gene
CARGCNAARCAYAARCARMGNAARMGNYTNAARWSNWSNTGYAARMGNCAYCCNYTNTAYGTNGAYTTYWSN
GAYGTNGGNTGGAAYGAYTGGATHGTNGCNCCNCCNGGNTAYCAYGCNTTYTAYTGYCAYGGNGARTGYGGN
TGGCCNCARWSNGAYMGNAAYCCNMGNTAYGGNAAYCAYGTNGTNYTNYTNYTNAARATGCARGTNMGNGGN
GCNGCNYTNGCNMGNCCNCCNTGYTGYGTNCCNACNGCNTAYGCNGGNAARYTNYTNATHWSNYTNWSNGAR
GARMGNATHWSNGCNCAYCAYGTNCCNAAYATGGTNGCNACNGARTGYGGNTGYMGN SEQUENCE ID37: Variant 3 mature gene
CARGCNAARCAYAARCARMGNAARMGNYTNAARWSNWSNTGYAARMGNCAYCCNYTNTAYGTNGAYTTYMGN
GCNGARMGNWSNATHGTNGCNCCNCCNGGNTAYCAYGCNTTYTAYTGYCAYGGNGARTGYGGNTGGCCNCAR
WSNGAYMGNAAYCCNMGNTAYGGNAAYCAYGTNGTNYTNYTNYTNAARATGCARGTNMGNGGNGCNGCNYTN
GCNMGNCCNCCNTGYTGYGTNCCNACNGCNTAYGCNGGNAARYTNYTNATHWSNYTNWSNGARGARMGNATH
WSNGCNCAYCAYGTNCCNAAYATGGTNGCNACNGARTGYGGNTGYMGN -continued

| Sequence Listing |
| --- |

SEQUENCE ID38: Variant 4 mature gene
CARGCNAARCAYAARCARMGNAARMGNYTNAARWSNWSNTGYAARMGNCAYCCNYTNTAYGTNGAYYTNMGN
GCNGARMGNWSNGTNYTNATHCCNGARACNTAYCARGCNAAYAAYTGYCARGGNGTNTGYCCNTTYCCNYTN
GCNGAYCAYYTNAAYWSNACNAAYCAYGCNATHGTNCARACNYTNGTNAAYWSNGTNAAYWSNAARATHCCN
AARGCNTGYTGYGTNCCNACNGCNTAYGCNGGNAARYTNYTNATHWSNYTNWSNGARGARMGNATHWSNGCN
CAYCAYGTNCCNAAYATGGTNGCNACNGARTGYGGNTGYMGN SEQUENCE ID39: Variant 5 mature gene
CARGCNAARCAYAARCARMGNAARMGNYTNAARWSNWSNTGYAARMGNCAYCCNYTNTAYGTNGAYYTNMGN
GCNGARMGNWSNGTNYTNATHCCNGARACNTAYCARGCNAAYAAYTGYCARGGNGTNTGYCCNTTYCCNYTN
GCNGAYCAYYTNAAYWSNACNAAYCAYGCNATHGTNCARACNYTNGTNAAYWSNGTNAAYWSNAARATHCCN
AARGCNTGYTGYGTNCCNACNGCNTAYGCNGGNAARYTNYTNATHWSNYTNWSNGARGARMGNATHWSNGCN
CAYCAYGTNCCNAAYATGGTNGTNGARGGNTGYGGNTGYMGN SEQUENCE ID40: Variant 6 mature gene
CARGCNAARCAYAARCARMGNAARMGNYTNAARWSNWSNTGYAARMGNCAYCCNYTNTAYGTNGAYYTNMGN
GCNGARMGNWSNGTNYTNATHCCNGARACNTAYCARGCNAAYAAYTGYCARGGNGTNTGYCCNTTYCCNYTN
GCNGAYCAYYTNAAYWSNACNAAYCAYGCNATHGTNCARACNYTNGTNAAYWSNGTNAAYWSNAARATHCCN
AARGCNTGYTGYGTNCCNACNGARYTNGCNGGNAARYTNYTNATHWSNYTNWSNGARGARMGNATHWSNGCN
CAYCAYGTNCCNAAYATGGTNGTNGARGGNTGYGGNTGYMGN SEQUENCE ID41: Variant 7 mature gene
CARGCNAARCAYAARCARMGNAARMGNYTNAARWSNWSNTGYAARMGNCAYCCNYTNTAYGTNGAYTTYWSN
GAYGTNGGNTGGAAYGAYTGGATHGTNGCNCCNCCNGGNTAYCAYGCNTTYTAYTGYCAYGGNGARTGYCCN
TTYCCNYTNGCNGAYCAYYTNAAYWSNACNAAYCAYGCNATHGTNCARACNYTNGTNAAYWSNGTNAAYWSN
AARATHCCNAARGCNTGYTGYGTNCCNACNGCNTAYGCNGGNAARYTNYTNATHWSNYTNWSNGARGARMGN
ATHWSNGCNCAYCAYGTNCCNAAYATGGTNGCNACNGARTGYGGNTGYMGN SEQUENCE ID42: Variant 8 mature gene
CARGCNAARCAYAARCARMGNAARMGNYTNAARWSNWSNTGYAARMGNCAYCCNYTNTAYGTNGAYTTYMGN
GCNGARMGNWSNATHGTNGCNCCNCCNGGNTAYCAYGCNTTYTAYTGYCAYGGNGARTGYCCNTTYCCNYTN
GCNGAYCAYYTNAAYWSNACNAAYCAYGCNATHGTNCARACNYTNGTNAAYWSNGTNAAYWSNAARATHCCN
AARGCNTGYTGYGTNCCNACNGCNTAYGCNGGNAARYTNYTNATHWSNYTNWSNGARGARMGNATHWSNGCN
CAYCAYGTNCCNAAYATGGTNGCNACNGARTGYGGNTGYMGN SEQUENCE ID43: Variant 9 mature gene
CARGCNAARCAYAARCARMGNAARMGNYTNAARWSNWSNTGYAARMGNCAYCCNYTNTAYGTNGAYTTYWSN
GAYGTNGGNTGGAAYGAYTGGATHGTNGCNCCNCCNGGNTAYCAYGCNTTYTAYTGYCAYGGNGARTGYCCN
TTYCCNYTNGCNGAYCAYYTNAAYWSNACNAAYCAYGCNATHGTNCARACNYTNGTNAAYWSNGTNAAYWSN
AARATHCCNAARGCNTGYTGYGTNCCNACNGCNTAYGCNGGNAARYTNYTNATHWSNYTNWSNGARGARMGN
ATHWSNGCNCAYCAYGTNCCNAAYATGGTNGTNGARGGNTGYGGNTGYMGN SEQUENCE ID44: Variant 10 mature gene
CARGCNAARCAYAARCARMGNAARMGNYTNAARWSNWSNTGYAARMGNCAYCCNYTNTAYGTNGAYTTYMGN
GCNGARMGNWSNATHGTNGCNCCNCCNGGNTAYCAYGCNTTYTAYTGYCAYGGNGARTGYCCNTTYCCNYTN
GCNGAYCAYYTNAAYWSNACNAAYCAYGCNATHGTNCARACNYTNGTNAAYWSNGTNAAYWSNAARATHCCN
AARGCNTGYTGYGTNCCNACNGCNTAYGCNGGNAARYTNYTNATHWSNYTNWSNGARGARMGNATHWSNGCN
CAYCAYGTNCCNAAYATGGTNGTNGARGGNTGYGGNTGYMGN SEQUENCE ID45: Variant 11 mature gene
CARGCNAARCAYAARCARMGNAARMGNYTNAARWSNWSNTGYAARMGNCAYCCNYTNTAYGTNGAYTTYWSN
GAYGTNGGNTGGAAYGAYTGGATHGTNGCNCCNCCNGGNTAYCAYGCNTTYTAYTGYCAYGGNGARTGYCCN
TTYCCNYTNGCNGAYCAYYTNAAYWSNACNAAYCAYGCNATHGTNCARACNYTNGTNAAYWSNGTNAAYWSN
AARATHCCNAARGCNTGYTGYGTNCCNACNGARYTNGCNGGNAARYTNYTNATHWSNYTNWSNGARGARMGN
ATHWSNGCNCAYCAYGTNCCNAAYATGGTNGTNGARGGNTGYGGNTGYMGN SEQUENCE ID46: Variant 12 mature gene
CARGCNAARCAYAARCARMGNAARMGNYTNAARWSNWSNTGYAARMGNCAYCCNYTNTAYGTNGAYTTYMGN
GCNGARMGNWSNATHGTNGCNCCNCCNGGNTAYCAYGCNTTYTAYTGYCAYGGNGARTGYCCNTTYCCNYTN
GCNGAYCAYYTNAAYWSNACNAAYCAYGCNATHGTNCARACNYTNGTNAAYWSNGTNAAYWSNAARATHCCN
AARGCNTGYTGYGTNCCNACNGARYTNGCNGGNAARYTNYTNATHWSNYTNWSNGARGARMGNATHWSNGCN
CAYCAYGTNCCNAAYATGGTNGTNGARGGNTGYGGNTGYMGN SIN47: Variant 1 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN -continued Sequence Listing AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYYTNMGNGCNGARMGNWSNGTNYTNATHCCNGARACNTAYCARGCNAAY
AAYTGYCARGGNGTNTGYGGNTGGCCNCARWSNGAYMGNAAYCCNMGNTAYGGNAAYCAY
GTNGTNYTNYTNYTNAARATGCARGTNMGNGGNGCNGCNYTNGCNMGNCCNCCNTGYTGY
GTNCCNACNGCNTAYGCNGGNAARYTNYTNATHWSNYTNWSNGARGARMGNATHWSNGCN
CAYCAYGTNCCNAAYATGGTNGCNACNGARTGYGGNTGYMGN SEQUENCE ID48 Variant 2 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYTTYWSNGAYGTNGGNTGGAAYGAYTGGATHGTNGCNCCNCCNGGNTAY
CAYGCNTTYTAYTGYCAYGGNGARTGYGGNTGGCCNCARWSNGAYMGNAAYCCNMGNTAY
GGNAAYCAYGTNGTNYTNYTNYTNAARATGCARGTNMGNGGNGCNGCNYTNGCNMGNCCN
CCNTGYTGYGTNCCNACNGCNTAYGCNGGNAARYTNYTNATHWSNYTNWSNGARGARMGN
ATHWSNGCNCAYCAYGTNCCNAAYATGGTNGCNACNGARTGYGGNTGYMGN SEQUENCE ID49 Variant 3 preprotein gene ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYTTYMGNGCNGARMGNWSNATHGTNGCNCCNCCNGGNTAYCAYGCNTTY
TAYTGYCAYGGNGARTGYGGNTGGCCNCARWSNGAYMGNAAYCCNMGNTAYGGNAAYCAY
GTNGTNYTNYTNYTNAARATGCARGTNMGNGGNGCNGCNYTNGCNMGNCCNCCNTGYTGY
GTNCCNACNGCNTAYGCNGGNAARYTNYTNATHWSNYTNWSNGARGARMGNATHWSNGCN
CAYCAYGTNCCNAAYATGGTNGCNACNGARTGYGGNTGYMGN SEQUENCE ID50 Variant 4 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYYTNMGNGCNGARMGNWSNGTNYTNATHCCNGARACNTAYCARGCNAAY
AAYTGYCARGGNGTNTGYCCNTTYCCNYTNGCNGAYCAYYTNAAYWSNACNAAYCAYGCN
ATHGTNCARACNYTNGTNAAYWSNGTNAAYWSNAARATHCCNAARGCNTGYTGYGTNCCN
ACNGCNTAYGCNGGNAARYTNYTNATHWSNYTNWSNGARGARMGNATHWSNGCNCAYCAY
GTNCCNAAYATGGTNGCNACNGARTGYGGNTGYMGN -continued Sequence Listing SEQUENCE ID51 Variant 5 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYYTNMGNGCNGARMGNWSNGTNYTNATHCCNGARACNTAYCARGCNAAY
AAYTGYCARGGNGTNTGYCCNTTYCCNYTNGCNGAYCAYYTNAAYWSNACNAAYCAYGCN
ATHGTNCARACNYTNGTNAAYWSNGTNAAYWSNAARATHCCNAARGCNTGYTGYGTNCCN
ACNGCNTAYGCNGGNAARYTNYTNATHWSNYTNWSNGARGARMGNATHWSNGCNCAYCAY
GTNCCNAAYATGGTNGTNGARGGNTGYGGNTGYMGN SEQUENCE ID52 Variant 6 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYYTNMGNGCNGARMGNWSNGTNYTNATHCCNGARACNTAYCARGCNAAY
AAYTGYCARGGNGTNTGYCCNTTYCCNYTNGCNGAYCAYYTNAAYWSNACNAAYCAYGCN
ATHGTNCARACNYTNGTNAAYWSNGTNAAYWSNAARATHCCNAARGCNTGYTGYGTNCCN
ACNGARYTNGCNGGNAARYTNYTNATHWSNYTNWSNGARGARMGNATHWSNGCNCAYCAY
GTNCCNAAYATGGTNGTNGARGGNTGYGGNTGYMGN SEQUENCE ID53 Variant 7 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYTTYWSNGAYGTNGGNTGGAAYGAYTGGATHGTNGCNCCNCCNGGNTAY
CAYGCNTTYTAYTGYCAYGGNGARTGYCCNTTYCCNYTNGCNGAYCAYYTNAAYWSNACN
AAYCAYGCNATHGTNCARACNYTNGTNAAYWSNGTNAAYWSNAARATHCCNAARGCNTGY
TGYGTNCCNACNGCNTAYGCNGGNAARYTNYTNATHWSNYTNWSNGARGARMGNATHWSN
GCNCAYCAYGTNCCNAAYATGGTNGCNACNGARTGYGGNTGYMGN SEQUENCE ID54 Variant 8 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN -continued

| Sequence Listing |
|---|

ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYTTYMGNGCNGARMGNWSNATHGTNGCNCCNCCNGGNTAYCAYGCNTTY
TAYTGYCAYGGNGARTGYCCNTTYCCNYTNGCNGAYCAYYTNAAYWSNACNAAYCAYGCN
ATHGTNCARACNYTNGTNAAYWSNGTNAAYWSNAARATHCCNAARGCNTGYTGYGTNCCN
ACNGCNTAYGCNGGNAARYTNYTNATHWSNYTNWSNGARGARMGNATHWSNGCNCAYCAY
GTNCCNAAYATGGTNGCNACNGARTGYGGNTGYMGN

SEQUENCE ID55 Variant 9 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYTTYWSNGAYGTNGGNTGGAAYGAYTGGATHGTNGCNCCNCCNGGNTAY
CAYGCNTTYTAYTGYCAYGGNGARTGYCCNTTYCCNYTNGCNGAYCAYYTNAAYWSNACN
AAYCAYGCNATHGTNCARACNYTNGTNAAYWSNGTNAAYWSNAARATHCCNAARGCNTGY
TGYGTNCCNACNGCNTAYGCNGGNAARYTNYTNATHWSNYTNWSNGARGARMGNATHWSN
GCNCAYCAYGTNCCNAAYATGGTNGTNGARGGNTGYGGNTGYMGN SEQUENCE ID56 Variant 10 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYTTYMGNGCNGARMGNWSNATHGTNGCNCCNCCNGGNTAYCAYGCNTTY
TAYTGYCAYGGNGARTGYCCNTTYCCNYTNGCNGAYCAYYTNAAYWSNACNAAYCAYGCN
ATHGTNCARACNYTNGTNAAYWSNGTNAAYWSNAARATHCCNAARGCNTGYTGYGTNCCN
ACNGCNTAYGCNGGNAARYTNYTNATHWSNYTNWSNGARGARMGNATHWSNGCNCAYCAY
GTNCCNAAYATGGTNGTNGARGGNTGYGGNTGYMGN SEQUENCE ID57 Variant 11 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYTTYWSNGAYGTNGGNTGGAAYGAYTGGATHGTNGCNCCNCCNGGNTAY
CAYGCNTTYTAYTGYCAYGGNGARTGYCCNTTYCCNYTNGCNGAYCAYYTNAAYWSNACN
AAYCAYGCNATHGTNCARACNYTNGTNAAYWSNGTNAAYWSNAARATHCCNAARGCNTGY
TGYGTNCCNACNGARYTNGCNGGNAARYTNYTNATHWSNYTNWSNGARGARMGNATHWSN
GCNCAYCAYGTNCCNAAYATGGTNGTNGARGGNTGYGGNTGYMGN -continued Sequence Listing SEQUENCE ID58 Variant 12 preprotein gene
ATGGTNGCNGGNACNMGNTGYYTNYTNGCNYTNYTNYTNCCNCARGTNYTNYTNGGNGGN
GCNGCNGGNYTNGTNCCNGARYTNGGNMGNMGNAARTTYGCNGCNGCNWSNWSNGGNMGN
CCNWSNWSNCARCCNWSNGAYGARGTNYTNWSNGARTTYGARYTNMGNYTNYTNWSNATG
TTYGGNYTNAARCARMGNCCNACNCCNWSNMGNGAYGCNGTNGTNCCNCCNTAYATGYTN
GAYYTNTAYMGNMGNCAYWSNGGNCARCCNGGNWSNCCNGCNCCNGAYCAYMGNYTNGAR
MGNGCNGCNWSNMGNGCNAAYACNGTNMGNWSNTTYCAYCAYGARGARWSNYTNGARGAR
YTNCCNGARACNWSNGGNAARACNACNMGNMGNTTYTTYTTYAAYYTNWSNWSNATHCCN
ACNGARGARTTYATHACNWSNGCNGARYTNCARGTNTTYMGNGARCARATGCARGAYGCN
YTNGGNAAYAAYWSNWSNTTYCAYCAYMGNATHAAYATHTAYGARATHATHAARCCNGCN
ACNGCNAAYWSNAARTTYCCNGTNACNMGNYTNYTNGAYACNMGNYTNGTNAAYCARAAY
GCNWSNMGNTGGGARWSNTTYGAYGTNACNCCNGCNGTNATGMGNTGGACNGCNCARGGN
CAYGCNAAYCAYGGNTTYGTNGTNGARGTNGCNCAYYTNGARGARAARCARGGNGTNWSN
AARMGNCAYGTNMGNATHWSNMGNWSNYTNCAYCARGAYGARCAYWSNTGGWSNCARATH
MGNCCNYTNYTNGTNACNTTYGGNCAYGAYGGNAARGGNCAYCCNYTNCAYAARMGNGAR
AARMGNCARGCNAARCAYAARCARMGNAARMGNYTNAARWSNWSNTGYAARMGNCAYCCN
YTNTAYGTNGAYTTYMGNGCNGARMGNWSNATHGTNGCNCCNCCNGGNTAYCAYGCNTTY
TAYTGYCAYGGNGARTGYCCNTTYCCNYTNGCNGAYCAYYTNAAYWSNACNAAYCAYGCN
ATHGTNCARACNYTNGTNAAYWSNGTNAAYWSNAARATHCCNAARGCNTGYTGYGTNCCN
ACNGARYTNGCNGGNAARYTNYTNATHWSNYTNWSNGARGARMGNATHWSNGCNCAYCAY
GTNCCNAAYATGGTNGTNGARGGNTGYGGNTGYMGN Nucleic Acid Key:
A = A
G = G
C = C
T = T (or U for RNA)
U = U
R = G or A
Y = T/U or C
M = A or C
K = G or T/U
S = G or C
W = A or T/U
B = G or C or T/U
D = A or G or T/U
H = A or C or T/U
V = A or G or C
N = A or G or C or T/U

We claim:

1. A protein comprising a chimera of bone morphogenic protein 2 (BMP2) and the Müllerian-inhibiting substance type II receptor (MISIIR)-binding region of the Müllerian-inhibiting substance (MIS) protein comprising an amino acid sequence selected from the group consisting of SEQ ID NO: 3, SEQ ID NO: 4, SEQ ID NO: 5, and SEQ ID NO: 6.

2. The protein of claim 1, wherein the chimera comprises an amino acid sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

3. A method for inducing apoptosis in a cell, comprising contacting the cell with the protein of claim 1 in an amount effective to stimulate the Müllerian-inhibiting substance type II receptor (MISIIR), thereby inducing apoptosis in the cell, wherein said cell expresses MISIIR, and wherein the cell is an ovarian cancer cell, an endometrial cancer cell, or a prostate cancer cell.

4. The method of claim 3, wherein the cell is an ovarian cancer cell.

5. The method of claim 3, wherein the protein is comprised in a composition comprising the protein and a carrier.

6. A method for inducing apoptosis in cells in a tumor, comprising administering to the tumor a composition comprising a pharmaceutically acceptable carrier and the protein of claim 1 in an amount effective to stimulate the Müllerian-inhibiting substance type II receptor (MISIIR) and an activin receptor-like kinase (ALK) in cells of the tumor that express the MISIIR and the ALK, thereby inducing apoptosis in said cells in the tumor, wherein the tumor is a tumor of the ovary, a tumor of the endometrium, or a tumor of the prostate gland.

7. The method of claim 6, wherein the tumor is a tumor of the ovary, a tumor of the ovary.

8. The method of claim 6, further comprising administering to the tumor a chemotherapeutic agent or irradiating the tumor.

9. A method for treating ovarian cancer, comprising administering to a patient in need thereof a composition comprising a pharmaceutically acceptable carrier and the protein of claim 1, thereby treating the ovarian cancer in the patient.

10. The method of claim 9, further comprising administering a chemotherapeutic agent to the patient or irradiating the ovarian cancer cells in the patient.

11. A kit comprising a composition comprising a pharmaceutically acceptable carrier and the protein of claim 1.

12. A composition comprising the protein of claim 1 and a carrier.

13. The protein of claim 1 comprising an amino acid sequence selected from the group consisting of SEQ ID NO: 20, SEQ ID NO: 21, SEQ ID NO: 22, and SEQ ID NO: 23.

14. The protein of claim 13, wherein the chimera comprises an amino acid sequence selected from the group consisting of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, and SEQ ID NO: 34.

15. A method for inducing apoptosis in a cell, comprising contacting the cell with the protein of claim 13 is an amount effective to stimulate the Müllerian-inhibiting substance type II receptor (MISIIR), thereby inducing apoptosis in the cell, wherein said cell expresses MISIIR and wherein the cell is an ovarian cancer cell, an endometrial cancer cell, or prostate cancer cell.

16. The method of claim 15, wherein the cell is an ovarian cancer cell.

17. The method of claim 15, wherein the protein is comprised in a composition comprising the protein and a carrier.

18. A method for inducing apoptosis in cells in a tumor, comprising administering to the tumor a composition comprising a pharmaceutically acceptable carrier and the protein of claim 13 in an amount effective to stimulate the Müllerian-inhibiting substance type II receptor (MISIIR) and an activin receptor-like kinase (ALK) in cells of the tumor that express the MISIIR and the ALK, thereby inducing apoptosis in said cells in the tumor, wherein the tumor is a tumor of the ovary, a tumor of the endometrium, or a tumor of the prostate gland.

19. The method of claim 18, wherein the tumor is a tumor of the ovary.

20. The method of claim 18, further comprising administering to the tumor a chemotherapeutic agent or irradiating the tumor.

21. A method for treating ovarian cancer, comprising administering to a patient in need thereof a composition comprising a pharmaceutically acceptable carrier and the protein of claim 13, thereby treating ovarian cancer in the patient.

22. The method of claim 21, further comprising administering a chemotherapeutic agent to the patient or irradiating the ovarian cancer cells in the patient.

23. A kit comprising a composition comprising a pharmaceutically acceptable carrier and the protein of claim 13.

24. A composition comprising the protein of claim 13 and a carrier.

* * * * *

UNITED STATES PATENT AND TRADEMARK OFFICE

CERTIFICATE OF CORRECTION

PATENT NO. : 11,261,225 B2
APPLICATION NO. : 16/483944
DATED : March 1, 2022
INVENTOR(S) : Roland L. Dunbrack et al.

It is certified that error appears in the above-identified patent and that said Letters Patent is hereby corrected as shown below:

On the Title Page

At item (71) Applicants:
Please delete "THE RESEARCH INSTITUTE OF FOX CHASE CANCER CENTER" and insert therefor --INSTITUTE FOR CANCER RESEARCH D/B/A/ THE RESEARCH INSTITUTE OF FOX CHASE CANCER CENTER--.

At item (73) Assignee:
Please delete "INSTITUTE FOR CANCER RESEARCH" and insert therefor --INSTITUTE FOR CANCER RESEARCH D/B/A/ THE RESEARCH INSTITUTE OF FOX CHASE CANCER CENTER--.

Signed and Sealed this
Seventeenth Day of May, 2022

Katherine Kelly Vidal

Katherine Kelly Vidal
*Director of the United States Patent and Trademark Office*